(12) United States Patent
Scott

(10) Patent No.: US 7,523,647 B2
(45) Date of Patent: Apr. 28, 2009

(54) MULTIPHASE FLUID CHARACTERIZATION

(75) Inventor: Bentley N. Scott, Garland, TX (US)

(73) Assignee: Phase Dynamics, Inc., Richardson, TX (US)

( * ) Notice: Subject to any disclaimer, the term of this patent is extended or adjusted under 35 U.S.C. 154(b) by 13 days.

(21) Appl. No.: 11/484,328

(22) Filed: Jul. 11, 2006

(65) Prior Publication Data

US 2007/0157708 A1    Jul. 12, 2007

Related U.S. Application Data

(60) Provisional application No. 60/698,056, filed on Jul. 11, 2005, provisional application No. 60/721,235, filed on Sep. 28, 2005.

(51) Int. Cl.
*G01N 33/20* (2006.01)

(52) U.S. Cl. .................. 73/61.44; 73/1.02; 73/32 R

(58) Field of Classification Search .................. 73/61.44
See application file for complete search history.

(56) References Cited

U.S. PATENT DOCUMENTS

| | | | |
|---|---|---|---|
| 5,259,239 | A | 11/1993 | Gaisford |
| 5,260,667 | A | 11/1993 | Garcia-Golding |
| 5,576,974 | A | 11/1996 | Marrelli et al. |
| 5,654,502 | A | 8/1997 | Dutton |
| 6,234,030 | B1 | 5/2001 | Butler |
| 6,318,156 | B1 | 11/2001 | Dutton et al. |
| 6,327,914 | B1 | 12/2001 | Dutton |
| 6,826,964 | B2 * | 12/2004 | Nyfors ............ 73/861.04 |
| 7,135,870 | B2 * | 11/2006 | Mohajer et al. ......... 324/639 |
| 2005/0081643 | A1 | 4/2005 | Mattar et al. | |

FOREIGN PATENT DOCUMENTS

WO    WO 00/77739 A1    12/2000

OTHER PUBLICATIONS

Friisø, Trond and Tjomsland, Tore. Monitoring of density changes in low-permittivity liquids by microwave-permittivity measurements with an open-ended probe. Measurement Science and Technology 1997 vol. 8 pp. 1295-1305.*

(Continued)

*Primary Examiner*—Hezron Williams
*Assistant Examiner*—Mark Shabman

(57) ABSTRACT

Methods for determining and validating a first phase fraction of a gravitationally-separated multiphase fluid by conducting physical and electrical property measurements on samples of the fluid. The water content of crude petroleum oil is determined after the oil and water have begun to separate into phase layers such as occurs during un-agitated holding of the crude petroleum oil. A series of measurements of electrical properties such as permittivity and physical properties such as density is collected. The density minima can be used to generate hindsight determinations of average properties, such as the dry oil phase density, which in turn can be used to increase the accuracy of the water percentage in the oil determined by the permittivity and density methods. Flow weighted averages of water percentages by each method can be used to determine and validate the water content of the crude petroleum oil.

21 Claims, 12 Drawing Sheets

OTHER PUBLICATIONS

Busadi Khamis Et al., "New Development in Water Cut Meter with Salinity Compensation", SPE Asia PAC Oil Gas Conf; SPE-Asia Pacific Oil and Gas Conference 2002, pp. 599-602.

Mehdizadeh P: "Test Verifies Water-Cut Meter Accuracy in Steamflood", Oil and Gas Journal, Pennwell, Houston, TX, US. Oct. 2, 2000, pp. 97-98, 100.

Means, S R et al. "New Technology Improves Portable Well Testing Units", Oil and Gas Journal, Pennwell, Houston, TX US. Oct. 30, 2000, pp. 36-38.

Dutton, Robert E., "Automatic Well Test System and Method of Operating the Same",PCT/US96/20890, Dec. 23, 1996,WO 97/24615,Jul. 10, 1997.

Xie, Cheng-Gang et al, "Method and Apparatus for Estimating Water Conductivity of Multiphase Mixtures", UK 2 376 074 A, May 30, 2001.

Mohajer, Kim et al, "Device for Determining Compositiion of a Fluid Mixture", PCT/US05/015341, Mar. 5, 2005, WO 2005/109012A1 Nov. 17, 2005.

* cited by examiner

MULTIPHASE FLUID CHARACTERIZATION

CROSS-REFERENCE TO RELATED APPLICATIONS

This application claims priority from U.S. Provisional Patent Application 60/698,056 filed on Jul. 11, 2005 and U.S. Provisional Patent Application 60/721,235 filed on Sep. 28, 2005.

BACKGROUND AND SUMMARY OF THE INVENTION

The present application generally relates to methods for measuring the amount of one phase in a mixture of phases, more particularly to measuring the amount of water present in crude petroleum oil, and most particularly to low water cut crude petroleum oils.

The following paragraphs contain some discussion, which is illuminated by the innovations disclosed in this application, and any discussion of actual or proposed or possible approaches in this Background section does not imply that those approaches are prior art.

Background: Water Cut Analyses in Oil Processing

The chemical and physical characterization of crude, partially refined, and fully refined petroleum products is a common practice in the petroleum industry. Characterizations such as compositional, electrical, and physical property determinations are used for a variety of purposes. One of their more important uses is when they are done in combination with oil well testing to assist in optimizing oil production from a single or series of oil wells. Another important use is during the transfer of crude petroleum oil, as occurs during the production, transport, refining, and sale of oil. Specifically, it is well known to a person having ordinary skill in the art of petroleum engineering that crude petroleum oil emerging from production wells can contain large amounts of water, ranging from generally about 1% to as high as about 99% water. This value is known as the water cut ("WC").

When water is pumped to the surface of the Earth along with crude petroleum oil, producers often attempt to physically separate the water from the oil, because the water can corrode pipes and damage down-stream processing equipment. Further, the water has no value relative to the oil and in-fact can become a disposal or environmental problem wherever it is finally removed. Water-oil "separators" or liquid-liquid decanters are thus often used, before the crude petroleum oil is further transported from a well site or tank farm. However, the efficiency of such separators in achieving two pure streams of oil and water is often not 100%, and free water is still frequently entrained in the crude petroleum oil as it enters storage, in the range of about 0.10% to about 5%.

The accurate determination of water content and validation of the amount of water in crude petroleum oil is particularly important during the taxation of crude petroleum oil and the sale of crude petroleum oil, where the owner or seller of the oil does not want to pay taxes on water and the customer does not want to pay the price of oil for water. Such determinations and validations can be conducted on-line and off-line during petroleum processing.

The offline method involves physically sampling the stream and analyzing it in a laboratory setting. In the petroleum industry, the sampling is usually done using a composite sampler which automatically opens a sample valve attached to a pipeline at some frequency to collect an aggregate sample into a sample container. The objective is to collect a sample which is representative of the entire lot of petroleum under consideration. After collection, the composite sample is usually picked up by a person and taken to a laboratory. The composite sample is then "sampled" to prepare aliquots, or sub-divisions of the composite sample, for each of the various characterizations, or analysis methods, to be used.

Three off-line analytical methods are commonly used for determining the water content of crude petroleum oil. These are the centrifuge method, the distillation method, and the titration method. See the American Petroleum Institute ("API") Manual of Petroleum Measurement Standards, Chapter 10. The distillation and titration methods are relatively accurate, but are plagued by long analysis times and not suitable for use in the field or at the point of sale. The centrifuge method is quicker, but almost always under-reports the amount of water present. The American Society for Testing of Materials has reported the standard analytical errors for water content measurements using the three methods. The repeatability errors are 0.11% for the distillation method (see ASTM D4006), 0.15% for the titration method (see ASTM D4377), and 0.28% for the centrifuge method (see ASTM D4007).

Note that composite petroleum samplers and the associated analytical methods have other kinds of problems and disadvantages other than, for example, meeting a desired accuracy for a given determination. For example, results for composite samplers are typically only available at the end of a batch or a test, and there is no recourse if something goes wrong with the sampling system during the sampling process. At the end of the sampling and analysis, only a single number is available to consider. Additionally, the exposure of personnel to hazardous liquids associated with processing the samples is undesirable. Thus, the petroleum industry has continued to seek other methods that provide the required accuracy, speed, and safety.

Accordingly, the use of rapid on-line instruments such as densitometers, capacitance probes, radio frequency probes, and microwave analyzers to measure water content of petroleum products is becoming more common. In addition to providing increasingly accurate determinations of water content, real time water content results via on-line methods can provide beneficial operational advantages. Knowledge of when water becomes present in petroleum as it is being produced and the magnitude of the quantity of the water may provide an opportunity to remove the water before it reaches a transport pipeline, storage vessel, or shipping tanker. Additionally, the real time data may show if the water is detected in several short periods of time or if it is present across the entire load of the petroleum. Furthermore, real time analyzers may be used as a comparison to the results provide by composite samplers. Finally, on-line measurements of, for example, physical and electrical properties, via instrumentation reduces the need human involvement in the process of characterizing a multiphase fluid mixture.

Background: Water Cut by the Density and Permittivity Methods

On-line densitometers can be used to ascertain the amount of water in petroleum oil. One on-line density method uses a Coriolis meter. This meter can be installed in the pipeline leaving the well or wells on the way to further processing and storage. Coriolis meters measure the density of a fluid or fluid mixture, and usually its mass flow rate as well, using the Coriolis effect. Then, calculations can be performed to indirectly determine the water percentage. For example, a Coriolis meter can measure the density of a water-oil mixture, $\rho_{mixture}$, and then perform a simple calculation method to determine the individual fractions or percentages of the water phase and oil phase. By knowing or assuming the density of the dry oil, $\rho_{dry\ oil}$, and the density of the water phase, $\rho_{water\ phase}$, then a water weight percentage, $\Psi_{water}$, can be calculated as follows:

$$\Psi_{water\ phase} = ((\rho_{mixture} - \rho_{dry\ oil})/(\rho_{water\ phase} - \rho_{dry\ oil})) \times 100$$

Note that the above equation can work equally well using the specific gravities of the mixture, dry oil, and water phase, where specific gravity is the ratio of the particular density to the density of water at 4 degrees Celsius.

It should be recognized that the water percentage by density method is subject to uncertainty. First, due to natural variations of, for example, the hydrocarbon composition of crude petroleum oil, the density of the dry oil can vary significantly from the assumed or inputted value required for the simple calculation. Such a value inputted into a densitometer based on a guess or on history of a given oil well. Crude petroleum oils can range from about 800 kilograms per cubic meter ($kg/m^3$) to about 960 $kg/m^3$. Further, the water encountered in oil well production is most often saline. This salinity is subject to variability, ranging from about 0.1% by weight salt to about 28%. This results in a variation in the density of the water phase from about 1020 $kg/m^3$ to about 1200 $kg/m^3$. Again, this value would be inputted into a densitometer based on a previously known laboratory number or on the history of a given well.

Note also that an entrained gas phase, as is sometimes present, can dramatically affect the density of a crude petroleum oil stream as measured by a Coriolis meter, unless a precise correction method is applied for the presence of the gas.

Another technique to determine the water percentage is to use a microwave analyzer, instead of a densitometer, to perform the in-line monitoring of the oil and water mixture.

U.S. Pat. No. 4,862,060 to Scott (the '060 patent), entitled Microwave Apparatus for Measuring Fluid Mixtures and which is hereby incorporated by reference, discloses microwave apparatuses and methods which are most suitable for monitoring water percentages when the water is dispersed in a continuous oil phase.

Note that the change in fluid mixture dielectric properties for a water and oil mixture can be affected by a number of parameters, including not only the percentage of water in oil, but also the individual dielectric constants of the oil phase and the water phase. For example, the dielectric constant of the dry crude petroleum oil itself can vary depending on its density and chemical composition. Note that temperature can affect the density of the oil and the water and thus the dielectric properties of each component and the mixture. However, temperature variations can easily be compensated for by using a temperature probe in-contact with the multiphase fluid being characterized to allow referencing to data sets or curves fit to the data sets for different temperatures.

Thus, both the densitometer method ("WC by density") and the permittivity method ("WC by permittivity") are subject to uncertainties. One approach to dealing with the uncertainty is to simultaneously use both methods to characterize a crude petroleum oil stream for water content. This joint use is practiced commercially. An example is the Compact Cyclone Multiphase Meter manufactured by Phase Dynamics, Inc. of Richardson, Tex.

When conducting joint densitometry and permittivity characterizations of a flow stream of mixtures of water and crude or partially refined petroleum oils, exact values of the electrical and physical properties of the pure water and oil phases are not always known. However, in certain situations, each method can supply estimates of some of the required values to assist each other in determining water content in petroleum products.

An example of a such a supply of a physical property estimate is disclosed in U.S. patent application Ser. No. 11/273,613 to Bentley N. Scott entitled Methods for Correcting On-Line Analyzer Measurements of Water Content in Petroleum, and is hereby incorporated by reference, and hereinafter referred to as Scott '3613. Scott '3613 discloses that because a conventional permittivity analyzer is usually shop-calibrated across a range of water contents using a dry oil of a known density, the analyzer will report an erroneous water percentage if the dry oil being measured in the field shifts to a different density than that of the original dry calibration oil. The auto-correction method disclosed in Scott '3613 ameliorates this problem. Scott '3613 teaches that there is 0.03% WC by permittivity error introduced for every 1 $kg/m^3$ shift in actual dry oil density from the dry oil calibration density. It discloses that for WC's less than about 5%, the density of the actual dry oil can be adequately estimated for use in calculations by the permittivity meter by assuming the actual dry oil density is equal to the density of the mixture as measured by the densitometer. This assumption results in a maximum error rate of about 0.23% at about 5% WC. This error rate compares favorably to the off-line analytical method error rates previously detailed.

Background: Crude Petroleum Oil Phase Behavior and Permittivity

Still further uncertainty in conducting characterizations of multiphase fluids such as crude petroleum oil can be caused by both the physical chemistry of each of the fluids and the multiphase fluid mixture itself. In the case of liquid-liquid mixtures undergoing mechanical energy input, the mixture usually contains a dispersed phase and a continuous phase. So, in the example of water and oil, the mixture exists as either a water-in-oil or an oil-in-water dispersion. When such a dispersion changes from aqueous phase continuous to non-aqueous phase continuous, or vice-versa, it is said to "invert the emulsion phase."

Dispersion of one phase into another becomes more stable under mechanical energy input such as agitation, shaking, shearing, or mixing. These resulting physical properties are known as the rheological properties of the fluids. When the mechanical energy input is reduced or eliminated, coalescing of the dispersed phase can occur, where droplets aggregate into larger and larger volumes. However, these can also be very stable with time depending upon the natural surfactants, densities, temperatures, and salinity of the water. Further, in a substantially static situation (e.g. reduced energy input), heavy phase "settling-out" or stratification can occur under the force of gravity.

Stratification of a lot of crude petroleum oil can lead to sampling difficulties. Processors will often attempt to mix the stratified liquids to allow more uniform sampling. Mixing of large volumes of stratified crude petroleum oil, say 4.1 million barrels contained in an ocean-going supertanker is impractical. Auto-sampling of such stratified volumes is usually done, but with the attending problems as previously described, the least of which is not the fact that samples can get lost, destroyed, spilled, or consumed during repeat testing.

A further complicating phase-state phenomena of liquid-liquid mixtures is that stable or semi-stable suspensions of dispersed-phase droplets can sometimes occur. This is usually referred to as an emulsion, which can be either stable or semi-stable. Certain substances are known as emulsifiers and can increase the stability of an emulsion, meaning that it takes a longer time for the emulsion to separate into two phases under the force of gravity or using other means. In the case of petroleum oils, emulsifiers are naturally present in the crude petroleum oil. For example, very stable emulsions can occur during petroleum processing, as either mixtures of water-in-oil or oil-in-water with the water-in-oil as a stable emulsion possible even up to 90% water.

Another complicating phenomena is that the formation of dispersions and emulsions are sometimes "path-dependent." Generally, path-dependence exists when the result of a process depends on its past history, i.e. on the entire sequence of operations that preceded a particular point in time, and not just on the current instantaneous conditions. In the case of emulsions, the process of forming the emulsion can be path dependent because the sequence of phase addition, mixing, and energy inputs can affect which phase becomes the dispersed phase and how stable the resulting emulsion is. Thus, if one does not know the history of the multiphase fluid undergoing dispersion or emulsification, one will not always be able to predict the "state" of the dispersion or emulsion, i.e. which phase is continuous and which is dispersed, even if the proportions of the phases are accurately known at a particular point in time.

For permittivity analyzers, whether a dispersion or emulsion is water-continuous or oil-continuous has a significant effect on the analyzer's measurements. In the case of water-continuous dispersions or emulsions, the conductivity path established by the water continuous phase causes a significant change in the measured permittivity relative to the same proportion of phases existing as an oil continuous dispersion or emulsion. Additionally, further variations in the conductivity of the aqueous or water continuous phase caused, for example, by even relatively small changes in salinity, can significantly affect the measured permittivity results. Note that when the non-aqueous or oil phase is continuous, no conductivity path is established (because the droplets are not "connected" to form a continuous conducting circuit) and hence there is no significant effect on the measurements of a permittivity analyzer due to the conductivity of the aqueous phase. Note also that this is only true when the wavelength of the electromagnetic energy is large compared to the emulsion size. When the emulsion size is larger than one eight of a wavelength the voltage difference across the emulsion can be significant and therefore a correction must be made with respect to the salinity (conductivity at the frequency of measurement) of the water.

As a particular example of the complex behavior of liquid-liquid mixtures and the impact of that behavior on electrical characterizations such as permittivity analyses, consider FIG. 1A. It is a generalized phase diagram 100 of a particular crude petroleum oil and a range of aqueous solutions of varying salinity where the fraction of the water phase, $X_W$, is plotted against the frequency, f, as instantaneously read by a microwave permittivity analyzer. Note that although the lines are shown as straight lines, the relationship between $X_W$ and f may not be strictly linear. To illustrate aspects of the complex behavior of liquid-liquid mixtures, consider starting with a pure oil phase that is under-going a given amount of mechanical energy input, as is encountered when such a fluid is pumped through a restricting valve and is experiencing a pressure drop. This starting composition, on the path independent, oil-continuous line 101, is represented by point 102. Then, an aqueous saline solution could be added to the oil phase to form a mixture of water-in-oil, represented by points on line 101. The relationship between the permittivity frequency and the aqueous phase fraction is determined by the line 101. On this line, the multiphase fluid exists as an oil continuous phase with drops of dispersed aqueous phase. Then, increasing amounts of saline solution can continue to be added, up along line 101 to point 104. At point 104, the dispersion progresses along path dependent line 105 to point 106. At point 106, the dispersion inverts to an aqueous phase continuous dispersion, with an accompanying discontinuity in measured permittivity, jumping to a particular permittivity curve depending to a large extent on the salinity of the aqueous phase. Aqueous phase can continue to be added along salinity iso-lines in zone 107 to path-independency transition level 108. At path-independency transition level 108, path dependency is no longer present as the dispersion moves into zone 109. The fraction of aqueous phase can be increased to 1.00, with the permittivity being dependent on both the salinity and the fraction of the aqueous phase.

It should be noted that in certain emulsions, zone 107 may not exist at all, and line 105 might transition directly to zone 109.

In an another example of possible path dependency, the mixture may begin as a point located some where in a high water cut, path independent, salinity-controlling, aqueous continuous zone 109. Then, the aqueous fraction could be reduced to path-dependency transition level 110, and further reduced to aqueous fraction 112, along the iso-salinity lines within the high water cut, path dependent, aqueous-continuous zone 111. The iso-salinity lines within zone 111 are shown as dashed lines because they represent salinity levels which may be the same as that in zone 107. Additionally, path-dependency transition level 110 may or may not be equal to path-independency transition level 108.

Following the iso-salinity lines through zone 107, the dispersion would invert at aqueous fraction 112, and as aqueous fraction is further reduced, the relationship follows oil-continuous, path-dependent line 113 to point 104.

It should be noted that in certain emulsions or dispersions, zone 111 may not exist at all, and line 113 might transition directly from zone 109.

Thus, for the particular crude petroleum oil example above as it is mixed in various proportions with a variable salinity aqueous phase, at least three zones of compositional uncertainty can exist for the permittivity of aqueous continuous dispersions, of which at least two such zones can be path-dependent. Additionally, at least three discrete curves can further relate the permittivity of oil-continuous mixtures, of which at least two such curves can be path dependent. In addition, the oil continuous region is dependant upon the frequency of operation as to whether salinity has any affect on the relationship with water percentage as described earlier with respect to the wavelength of the electromagnetic energy.

Such complex physical chemistry leads to numerous uncertainties with regards to permittivity-based composition determinations. For example, referring again to FIG. 1A of this application, frequency 114 can in-fact represent two different mixture compositions, 116 and 118, depending on how such compositions were formed, as previously described. Additionally, a particular aqueous fraction 119 can correspond to either an aqueous phase dispersion of varying salinity contents, points 120, each having a corresponding permittivity frequency (not shown) or an oil-continuous phase dispersion of a particular frequency 122.

It has been found that these compositional and permittivity frequency uncertainties can be reduced by using a number of methods, depending somewhat on which zone or curve the mixture state resides in or on. For example, to address the problems of phase inversion uncertainties in aqueous and non-aqueous multiphase mixtures, U.S. Pat. No. 4,996,490 to Scott (the '490 patent), entitled Microwave Apparatus and Method for Measuring Fluid Mixtures and which is hereby incorporated by reference, discloses microwave apparatuses and methods for accommodating phase inversion events. For the example of oil and water mixtures, the '490 patent discloses that whether a particular mixture exists as an oil-in-water or a water-in-oil dispersion can be determined using differences in the reflected and lost microwave power curves in the two different states of the same mixture. Therefore, the '490 patent disclose microwave apparatuses and methods, including the ability to measure microwave radiation power loss and reflection to detect the state of the dispersion. In further embodiments of that invention, methods are disclosed to compare the measured reflections and losses to reference reflections and losses to determine the state of the mixture as either water-in-oil or oil-in-water, which then allows the proper selection and comparison of reference values relating the measured microwave oscillator frequency to the percentage water. An embodiment of the '490 patent is reproduced from that patent in FIG. 1B, which explained and described in detail later in this Application.

Thus, referring again to FIG. 1A of this application, for water fraction 119, the apparatus and the method of the '490 patent would be able to identify whether the dispersion is in zone 111 or on line 105. When the composition is on line 105, microwave analyzers using the method of the '490 patent are able to accurately determine the aqueous phase fraction.

Thus, solving the problem of accurately ascertaining and validating the amount of each phase in multiphase mixtures is a long felt requiring a more complete and automated solution. More particularly, there is an increasing need for reduction of uncertainty in the characterization of petroleum as the value of petroleum continues to rise.

MULTIPHASE FLUID CHARACTERIZATION

Some examples of the present innovations are methods and systems for determining the amount of water in crude petroleum oil. As crude petroleum oil is held over time, gravitationally-induced separation of water-continuous and oil-continuous phases can occur. At least some of the properties of the separated phases can be used to generate water and oil property values which in turn can be used to provide improved water percentage determinations of crude petroleum oil.

In some embodiments (but not necessarily all), the disclosed ideas are used to determine the water fraction and the oil fraction in an oil and water mixture which has been subjected to gravity and un-agitated storage.

In some embodiments (but not necessarily all), the disclosed ideas are used for characterization of crude petroleum oil being off-loaded from a transport tanker, in which some gravitationally-induced phase separation of a water-continuous phase and an oil-continuous phase has occurred in the hold during transit.

In some embodiments (but not necessarily all), the disclosed ideas are used for characterization of crude petroleum oils being pumped from a storage vessel, in which some gravitationally-induced phase separation of a water-continuous phase and an oil-continuous phase has occurred in the tank during storage.

In some embodiments (but not necessarily all), the disclosed ideas are used to determine the water fraction and the oil fraction in a stored oil and water mixture which has been subjected to minimal mechanical energy input.

The disclosed innovations, in various embodiments, provide one or more of at least the following advantages:

Some of the disclosed inventions provide validation methods and systems using two different water determination methods to improve the confidence level in determining the amount of water in crude petroleum oil.

Some of the disclosed inventions provide calibration or correction methods and systems to improve the characterization of a crude or partially refined petroleum oils using a single multiphase fluid characterization system.

Some of the disclosed inventions provide calibration or correction methods and systems to reduce the uncertainty caused by the variable density of different dry petroleum oils and different water phases encountered during crude petroleum oil production and handling.

Some of the disclosed inventions provide methods and systems to avoid the need to mix a non-homogenous or separated multiphase fluid to obtain an accurate determination of the fraction of a first phase in a multiphase fluid.

Some of the disclosed inventions provide more accurate physical or electrical property measurements.

Some of the disclosed inventions provide near-real-time reduction of errors and supply more accurate results to aid in near-real-time decision-making or automatic flow diversion, without requiring oil stream sampling or off-line lab-work conducted on such samples and thus eliminating the cost, lost opportunities, and hazards associated with such sampling.

BRIEF DESCRIPTION OF THE DRAWINGS

The disclosed inventions will be described with reference to the accompanying drawings, which show illustrative, non-limiting embodiments of the invention and which are incorporated in the specification hereof by reference, wherein.

DETAILED DESCRIPTION OF THE PREFERRED EMBODIMENTS

The disclosed innovations of the present application will be described with particular reference to presently preferred embodiments (by way of example, and not of limitation).

Herein this application, a fraction of the multiphase fluid refers to a numerical value corresponding to a weight or volume percentage or fraction of the fluid, such as 85% being 0.85, for example.

Herein this application, a portion of the multiphase fluid refers to an amount of the multiphase fluid that is something less than the whole of the quantity of the multiphase fluid, and for which the precise numerical fraction of the multiphase fluid is not sought by the present innovations.

Herein this application, a phase of a multiphase fluid refers to a particular phase such as a liquid phase, gas phase, or solid phase. Additionally herein this application, a phase of a multiphase fluid also refers to a particular liquid phase in a multiphase fluid of two or more liquid phases, with or without a gas phase or phases. Additionally herein this application, a phase of a multiphase fluid also refers to a gas phase in a multiphase fluid of two or more liquid phases.

Herein this application, exploiting a measurement refers to the advantageous use of a measurement in further calculations, measurements, determinations, decisions, comparisons, or validations, or various combinations thereof.

Figure 1:
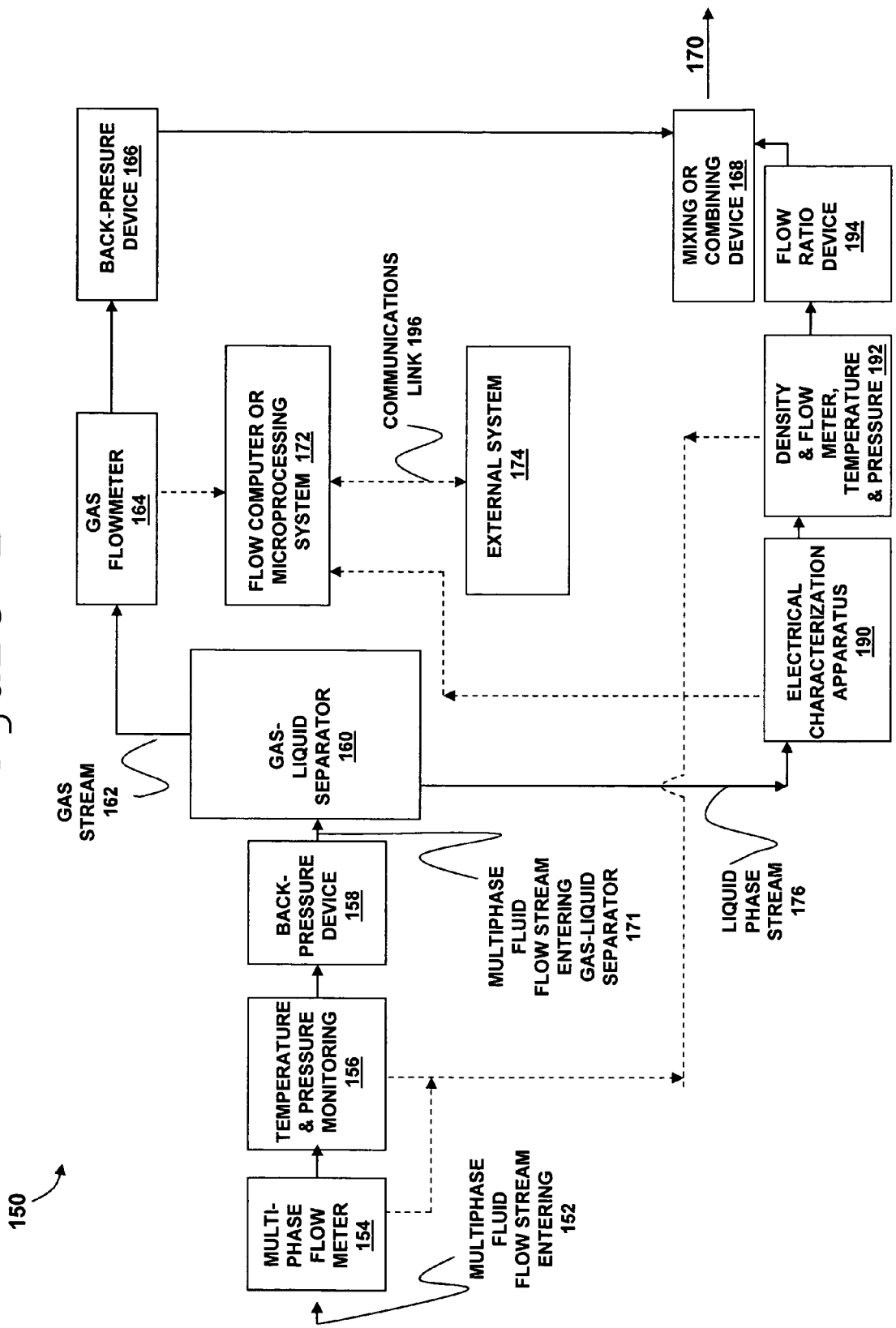
FIG. 1 shows an exemplary multiphase fluid characterization system comprising a liquid-gas separator, an electrical characterization system, a densitometer, flow meters, and a computer or microprocessor system incorporating the methods of FIGS. 3 and/or FIG. 4 and/or the method of FIG. 5, consistent with a preferred embodiment or embodiments.

FIG. 1 shows a characterization system 150 according to an illustrative, non-limiting example of a preferred embodiment consistent with the present application, for characterizing a multiphase fluid, such as crude petroleum oil. The crude petroleum oil can be a liquid stream comprising oil (referred to as the second component) and an aqueous solution (referred to as the first component), with entrained non-condensed gas. A gas-liquid-liquid multiphase fluid flow stream 152 can enter the system. The flow rate of the flow stream can be monitored at 154. Temperature and pressure of the flow stream can be monitored at 156. Back pressure of the flow stream can be maintained by a suitable device at 158. As discussed below, many different combinations of mechanical devices and instruments can be used. Multiphase flow stream 171 can emerge from the backpressure device of 158 and can enter gas-liquid separator 160 where a condensible and/or non-condensible gas fraction can be separated from the multiphase fluid to a degree consistent with the composition and physical properties of the multiphase fluid and its components, as well as the design and operating parameters of gas-liquid separator 160 as known to a person having ordinary skill in the design and operations of gas-liquid separators. The gas fraction flow stream 162 exits separator 160 and the flow rate, temperature, and pressure can be monitored at 164. Back pressure of flow stream 162 can be maintained by a suitable device at 166.

Gas-liquid production separators are described in Chapter 12 of the third printing of the Petroleum Engineering Handbook, Howard B. Bradley editor-in-chief, Society of Petroleum Engineers, 1992, hereby incorporated by reference. FIGS. 12.23 and 12.25 from the Petroleum Engineering Handbook show schematics of typical production gas-liquid separators.

A liquid-liquid fraction flow stream 176 can be electrically measured for water content at 190 and can be monitored for density, flow rate, temperature, and pressure at 192. The proper representative flow rate ratio of stream 176 to stream 162 can be maintained on stream 176 by a suitable device at 194.

Stream 176 and 162 can be combined in mixing or combining device 168 and then exit system 150 as stream 170.

Figure 3:
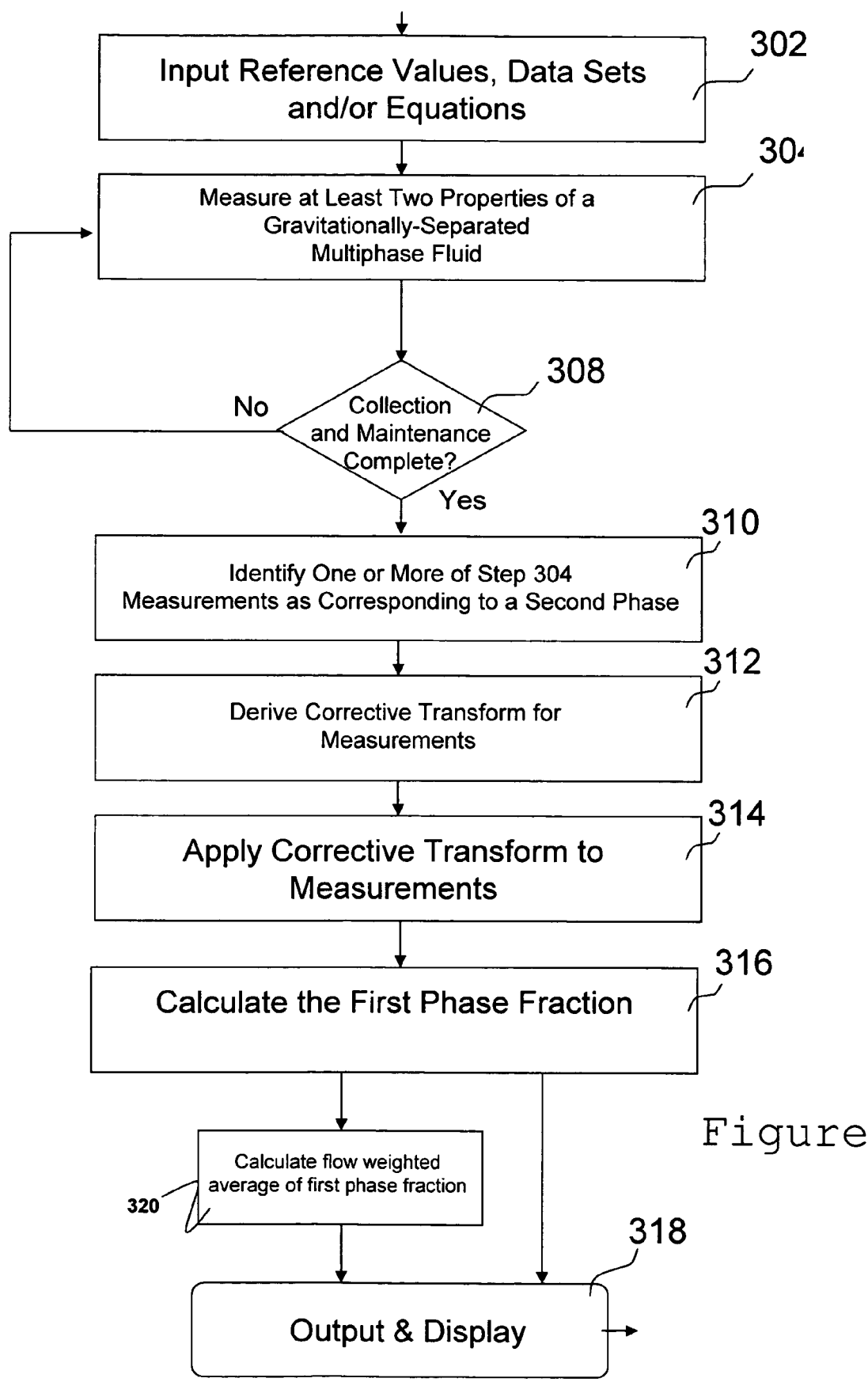
FIG. 3 shows a method for use with the system of FIG. 1 and FIG. 1B for determining the water cut of crude petroleum oil that has been subjected to gravitationally-induced separation, consistent with a preferred embodiment.
Figure 4:
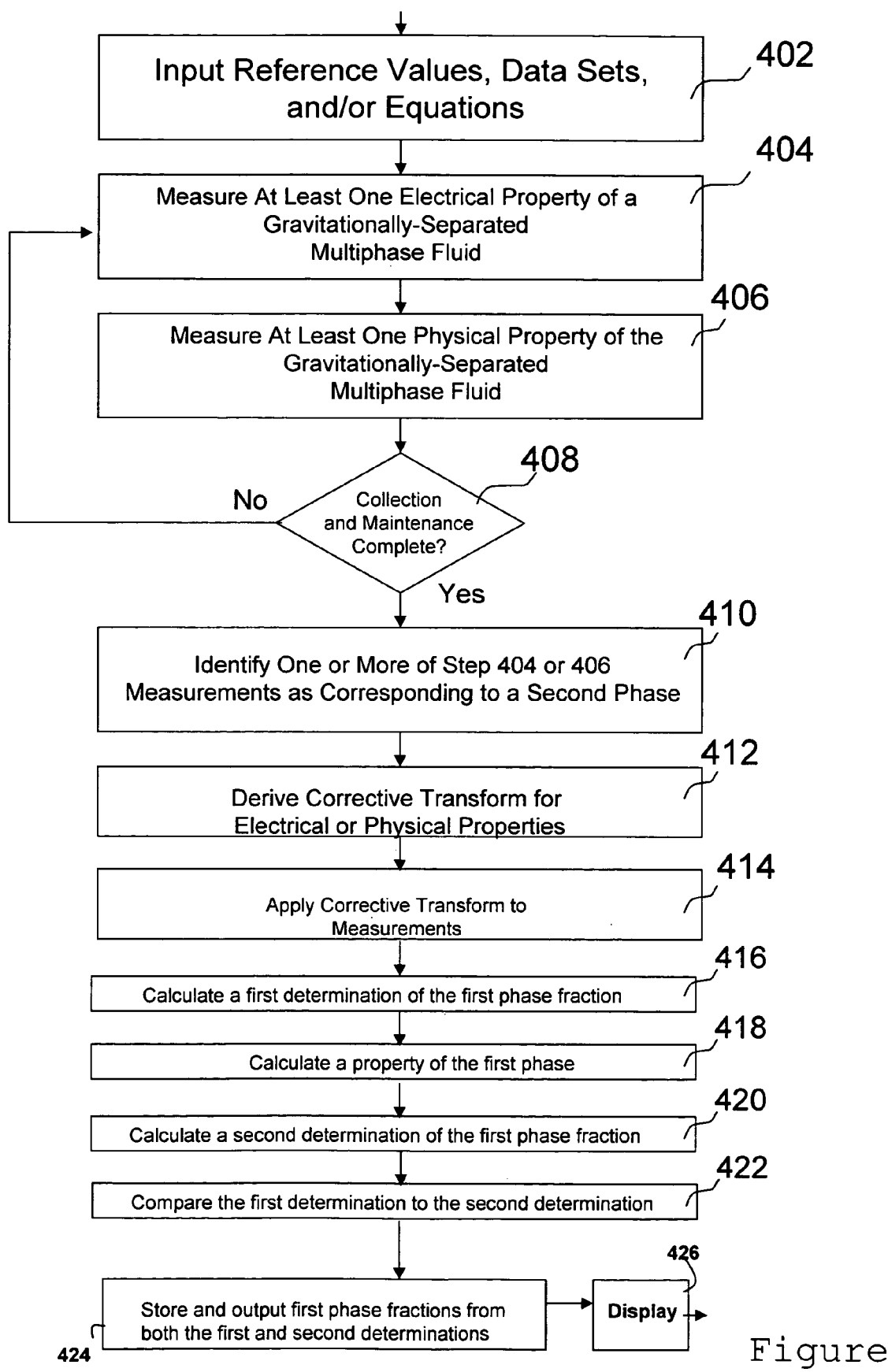
FIG. 4 shows one embodiment of a method used in the system of FIG. 1 and FIG. 1B for validating the water cut of crude petroleum oil that has been subjected to gravitationally-induced separation, consistent with a preferred embodiment.

Measuring components 154, 156, 190, 192, and 164 can all or selectively be electrically coupled (shown as dashed lines on FIG. 1) to flow computer or microprocessor system 172 which in one embodiment, performs and outputs the calculations of, for example, the methods of FIGS. 3, 4, and/or 5. In another embodiment, flow computer or microprocessor system 172 can transmit or output and display collected measurements to external system 174 where the measurements can be stored or other calculations can be performed, including, for example, the methods of FIGS. 3, 4, and/or 5.

Figure 1A:
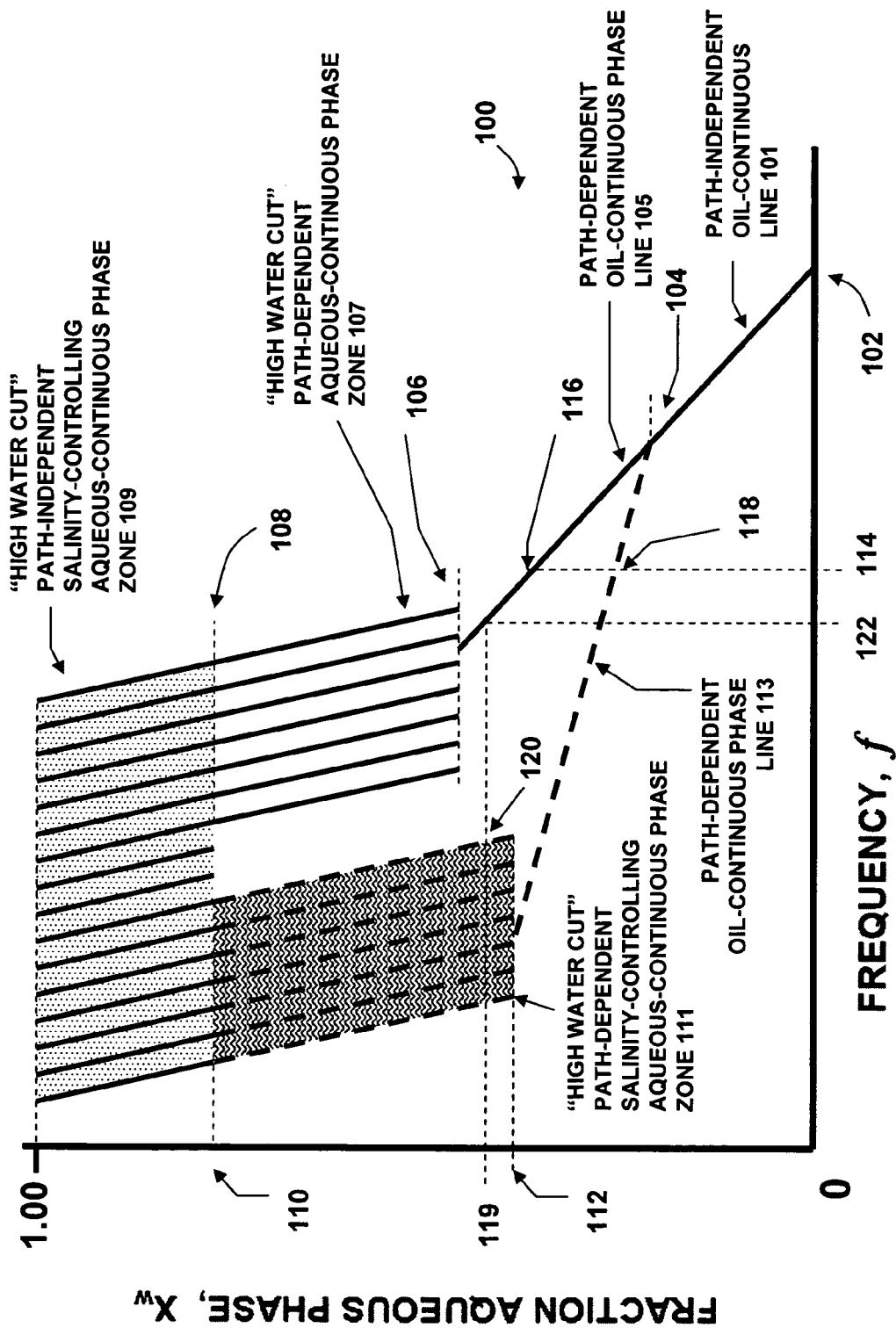
FIG. 1A shows a exemplary phase versus frequency diagram 100 of a particular crude petroleum oil and a range of aqueous solutions of varying salinity as previously described.

A water cut electrical characterization system can perform the function of water content measurement in component 190. U.S. Pat. No. 4,996,490 describes preferred some of the preferred embodiments of such a water cut electrical characterization system to be used in the present application. FIG. 1A is a reproduction of FIG. 1 from U.S. Pat. No. 4,996,490 as an example of one embodiment of a permittivity analyzer that can be used with the present innovations.

Figure 1B:
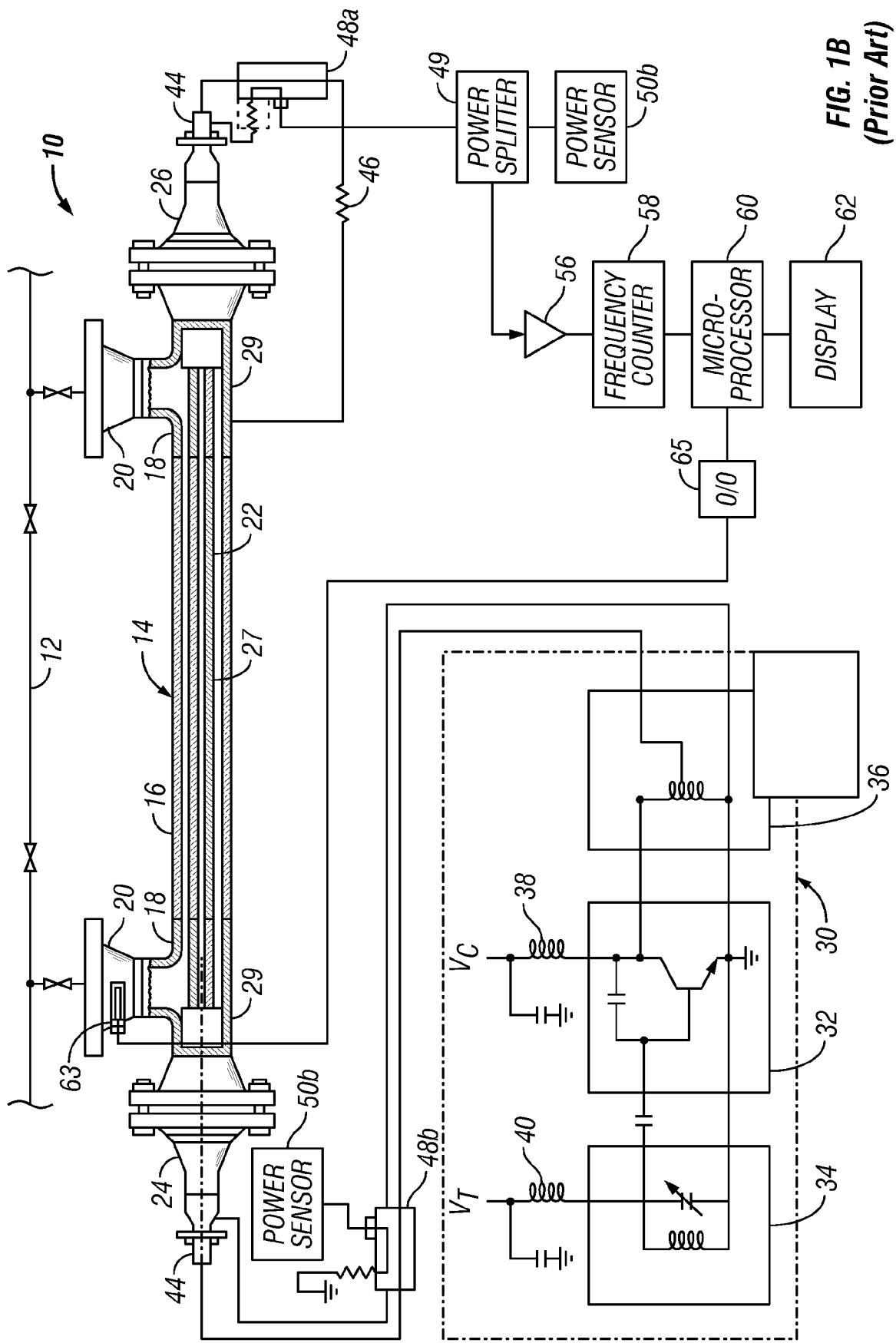
FIG. 1B shows a reproduction of U.S. Pat. No. 4,996,490 FIG. 1 as an example of one embodiment of an electrical characterization apparatus that can perform a water content analysis on a multiphase fluid flow stream.

FIG. 1B shows illustrated a diagram of an apparatus for measuring the concentration of one substance or material such as water, in another substance or material such as crude petroleum oil, which is being transmitted as a liquid mixture flow stream through a pipeline. The apparatus is generally designated by the numeral 10 and is particularly adapted for interconnection with a fluid transmission pipeline 12 for sampling the pipeline flow stream. Alternatively, the apparatus 10 might become part of the pipeline. The apparatus 10 includes a fluid flow conducting and measurement section 14 comprising an outer conduit section 16, including spaced apart pipe tee sections 18 having conventional flange portions 20 formed thereon for connection to branch conduit portions of the pipeline 12. The measurement 14 comprises a coaxial transmission line which includes a center conductor 22 preferably formed of a metal such as stainless steel which extends between opposed end support parts 24 and 26 which are described in detail in the above-referenced patent application. The center conductor 22 preferably comprises a generally cylindrical rod or tube member coaxially arranged in the conduit 16 and provided with an outer sheath 27 formed of a material having a relatively low dielectric loss tangent, preferably less than 0.1 at a frequency of 1.0 GHz. The sheath 27 preferably comprises a relatively easy-to-fabricate plastic such as polypropylene, a plastic sold under the trademark Delrin or one of the fluorocarbon plastics. Alternatively, certain ceramics or other materials may also be used as the outer sheath 27 as long as they are low loss tangent dielectric materials. The fit between the outer sheath 27 and the center conductor 22 is preferably a forced or line-to-line fit although some clearance may be permitted as long as fluid flow between the center conductor and the outer sheath is prohibited. In an apparatus where the center conductor has a diameter of 0.25 inches, the outer diameter of the sheath 27 is preferably at least about 0.50 inches or, alternatively, a ratio of the outer diameter of the sheath to the outer diameter of the center conductor is in the range of about two to one.

It has been determined that with the provision of a sheath 27 formed of one of the above-mentioned materials and in the proportions described, that the electrical circuit for propagating microwave radiation through the apparatus 22 retains a high quality signal resolution characteristic in liquid mixtures of oil and water, for example, wherein the water content is relatively high, that is on the order of more than 5% to 10% by volume. With this type of center conductor arrangement, the circuit associated with the apparatus 10 and described hereinbelow retains good field intensity or prevents short circuiting of the center conductor to the outer conductor in an unwanted location, the oscillator circuit retains its good load-pulling characteristics with good resolution of phase and the interface between the sheath 27 and the fluid in the conduit 16 is a new propagation medium which has desirable operating characteristics.

When the apparatus 10 is operating with a liquid composition which is high in water content or a so-called water continuous phase, the conductivity of the composition is high compared to a good dielectric but low compared to a good conductor and, of course, the liquid composition is in direct contact with the wall surfaces of the measurement section 14 including the center conductor. The insulating sheath 27 prevents the radio frequency (RF) energy from being shorted out immediately at the point where the RF energy enters the measurement section or where the fluid cross section begins. Moreover, the sheath 27 now becomes the primary region where the RF field is propagated with the conductive fluid becoming a pseudo outer wall of the measurement section in place of the wall of the conduit 16. The cross sectional measurement of the water-in-oil composition is still preserved due to the large skin depth of the microwave or RF energy at the operating frequency. This skin depth is large through the water as the conducting medium of the outer half of the coaxial transmission line formed by the measurement section. The dielectric structure is now the sheath 27. The properties of the propagated RF energy still reflect the changing content of the oil in the water and this is related through pulling of the unisolated oscillator which is described hereinbelow. The sheath 27 must be thick enough to maintain a reasonable coaxial impedance to be able to propagate the RF energy into the measurement section 14 and maintain a measurement capability. A very thin dielectric coating on the center conductor 22 will cause a very low impedance with a liquid composition having a high water content and therefore the RF energy would be reflected at the fluid interface.

RF energy is not propagated in the interior of a good conductor. The conductor guides the electromagnetic waves. The energy travels in the region between the conductors in a coaxial transmission system with a good dielectric. The currents that are established at the conductor surfaces propagate into the conductor in a direction perpendicular to the direction of the current density. The current density or electric field intensity established at the surface of a good conductor decays rapidly looking into the conductor. When the conductor is resistive or, low conductivity, this depth into the conductor increases rapidly. This phenomenon is known in the art as skin depth.

As shown in FIG. 1, the center conductor 22 extends through opposed end block members 29 which are also preferably formed of a relatively high insulative material such as a fluorocarbon plastic and the end plug sections are configured in a way similar to the ones described in the above-referenced patent application.

The measurement section 14 is operably connected to a source of radio frequency (RF) or so-called microwave energy comprising an unbuffered or unisolated, free-running oscillator, generally designated by the numeral 30. The oscillator 30 includes an active circuit 32 operably connected to a tuning circuit 34 and to an impedance matching network circuit 36. The circuit 32 is adapted to receive a constant DC voltage, $V_c$, from a source not shown and by way of a filter circuit 38. The tuning circuit 34 is also adapted to receive a controllable DC voltage, $V_t$, from another source, not shown, by way of a second filter circuit 40. The oscillator 30 has an appreciable load-pulling characteristic. The fundamental operating frequency of the oscillator is changed as the complex load is changed on the output circuit of the oscillator. The oscillator 30 is preferably of a type commercially available such as from Avantek Company, Santa Clara, Calif. as their model VTO 8030 voltage controlled oscillator. The exemplary oscillator 30 has a maximum load-pulling characteristic of about 35 MHz at a nominal 200 MHz operating frequency into all phases of a short circuit at the end of a 50 Ohm line stretcher (approximately 0.5 DB return loss). The oscillator 30 is operably connected to the apparatus measurement section 14 through a suitable connector 44 which is in electrically conductive engagement with the center conductor 22 at the end part 24 and at the opposite end of the center conductor 22 through a second connector 44, a resistance 46 and with the outer conductor or conduit 16 as illustrated. The end part 26 is also adapted to connect the center conductor 22 with a 10 DB directional coupler 48a which is operable to sample the microwave energy or power transmitted through the coaxial measurement section 14. The coupler 48a is connected to a power splitter 49 which is connected to a power sensor 50a. The directional coupler 48a may be of a type manufactured by Minicircuits Company of Brooklyn, N.Y. as their model ZED-15-2B. The power splitter 49 may be of a type ZFSC-2-2 also manufactured by Minicircuits. The power sensor 50 may be of a type 437B manufactured by Hewlett Packard of Sunnyvale, Calif.

A second directional coupler 48b is interposed in the circuit between the end part 24 and the oscillator 30 and is connected to a second power sensor 50b. The directional couplers 48a and 48b may be of identical configuration. The coupler 48a is connected to the power splitter 49 which provides an output signal which is amplified by an amplifier 56. The output of the amplifier 56 is adapted to be input to a frequency counter 58 which is also adapted to be connected to a microprocessor 60. A suitable digital display or readout device 62 is connected to the microprocessor 60. The amplifier 56 may be of a type commercially available from the above-mentioned Minicircuits Company as their model ZFL-500. The frequency counter 58 may be of a type manufactured by Hewlett Packard Company as their model 5342A and the microprocessor 60 may be a Hewlett Packard type 9836. The system illustrated in FIG. 1 preferably includes a temperature compensation circuit including a thermocouple 63 operably connected to a conversion circuit 65 to provide a suitable digital signal to the microprocessor 60.

In operation, the changing dielectric constant presented by the material flowing through the measurement section 14, such as caused by the presence in a liquid mixture, for example, of varying amounts of water in oil or oil in water, causes the oscillator 30 to change its operating frequency over a relatively narrow frequency band as compared with the nominal operating frequency of the oscillator. For example, the oscillator 30, in a preferred form, can be pulled from its nominal operating frequency through a range of about 20 MHz by the changing dielectric constant of the medium flowing through the measurement section 14.

Figure 2:
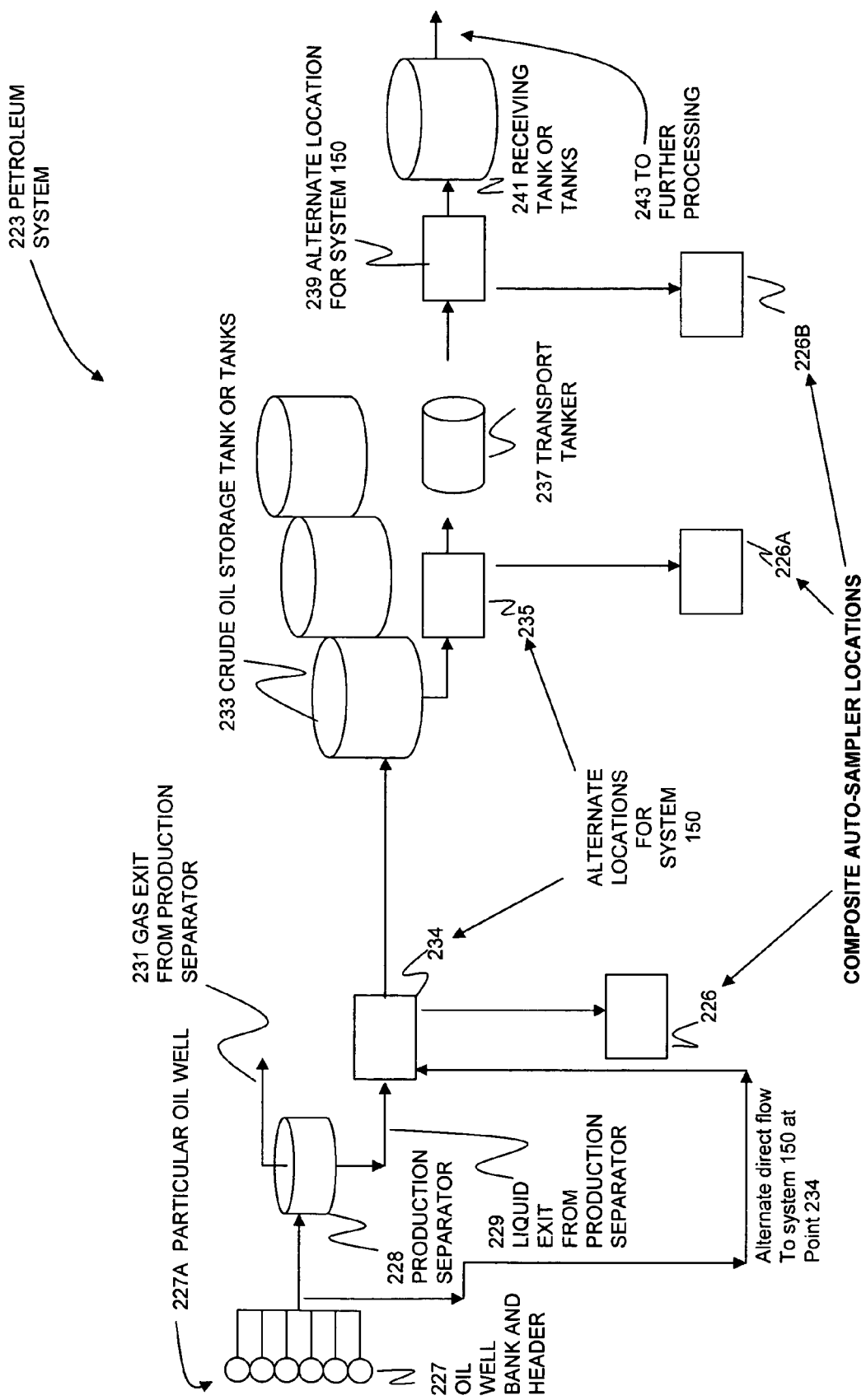
FIG. 2 shows an exemplary petroleum processing and transportation system, including wells, a pipeline, a pipeline header, a storage tank prior to transport, a transport tanker, and a receiving storage tank in which the multiphase fluid characterization system from FIG. 1 is incorporated at various locations, consistent with a preferred embodiment.

FIG. 2 shows an exemplary petroleum production, processing, characterization, and transportation system 223 according to an illustrative, non-limiting embodiment consistent with the present application in which the multiphase fluid characterization system 150 can be incorporated at numerous points, depending on the desired characterization. A pipeline leads from a set of petroleum-producing wells 227 or a given well 227A which all or some may be located on land or under-sea. The pipeline can lead to a production oil-gas separator 228. Stream 229 represents the separated liquid phase leaving the liquid-gas separator 228 whereas stream 231 is the separated gas leaving the separator. The multiphase fluid characterization system 150 can be positioned at point 234 between oil-water separator 228 and a storage tank or tanks 233. An auto-composite sampler 226 can be positioned either before or after system 150 at point 234. The pipeline can alternatively lead directly to system 150, by-passing production oil-gas separator 228, which can be located after point 234. The contents of storage tank 233 can optionally be loaded into transport tanker 237, which could be transported by rail, roadway, or water, which can then be unloaded from the transport tanker 237 to receiving storage tank or tanks 241. The multiphase fluid characterization system 150 can also be placed at points 235 or 239 to characterize the petroleum as it is either loaded and/or unloaded from a transport tanker. Auto-sampler 226 can be positioned before or after points 235 or 239 using point 226A or point 226B, respectively.

FIG. 3 shows a method according to one embodiment of the disclosed innovations for determining a first phase fraction of a gravitationally-separated multiphase fluid. In one embodiment, reference values, data sets, or equations which have been fitted, or parameters that have been fitted to those values or data sets are inputted for use in the development of corrective transforms by computer or microprocessor system 172 (step 302). In one embodiment, the method of FIG. 3 requires that electrical measurements of the first component fraction from electrical characterization apparatus 190 be read and collected (step 304). In one embodiment, densitometer measurements of the mixture density and the flow rates of the multiple-component fluid stream measured by the on-line densitometer 192 can be read and stored (step 304). In other embodiments, other electrical properties (step 304) and physical or non-electrical properties (step 304) can be read and collected for other kinds of characterizations of the multiphase fluid mixture. All of these values can then be stored in the memory of the computer or microprocessor system 172 and can then be used to implement data transformation methods. In one embodiment, the values can also be communicated to an external system 174 via link 196 for various operations such as storage, processing, data manipulation, transform development, and correction of raw data via the transforms by implementing the method of FIG. 3 on external system 174. In one embodiment in which a certain amount of a crude petroleum oil is characterized by system 150 using the method of FIG. 3, the method can check to see if the collection and maintenance of data is complete (step 308). If not, the method can repeat by returning to step 304 to collect more measurement values. Then, in another embodiment, at the end of, for example, a transfer period, as decided by step 308, those values can be recalled to identify one or more of the measurements as corresponding to a second phase (step 310). Then, a corrective transform can be derived (step 312). Then, the corrective transform can be applied to at least one of the plurality of measurements (step 314). Then, the method of FIG. 3 can calculate the first phase fraction (step 316) and outputs the results (step 318). In one embodiment, flow weighted averages for the fraction of the first and second phases are calculated, stored, and displayed (step 320 followed by step 318).

FIG. 4 shows a method according to one embodiment of the disclosed innovations for validating a first determination of a first phase fraction of a gravitationally-separated multiphase fluid. In one embodiment, reference values, data sets, parameters, or equations which have been fitted to those values or data sets are inputted for use in the development of corrective transforms by computer or microprocessor system 172 (step 402). In one embodiment, densitometer measurements of the mixture density and the flow rates of a crude petroleum oil stream measured by the on-line densitometer 192 can be read and stored (step 406) as measurements of a first property of the multiphase fluid. In one embodiment, the method of FIG. 4 requires that the on-line electrical characterization apparatus 190 electrical measurements of water content be read and collected (step 404) as measurements of a second property of the multiphase fluid. All of these values can then be stored in the memory of the computer or microprocessor system 172 and then be used to implement data transformation methods. In one embodiment, the values can also be communicated to an external system 174 via link 196 for various operations such as storage, processing, data manipulation, transform development, and correction of raw data via the transforms by implementing the method of FIG. 4 on external system 174. In one embodiment, step 410 can identify a densitometer measurement as corresponding to the density of the second phase of the multiphase fluid, such as the density of a dry oil phase. In one embodiment, step 412 can derive a corrective transform from the identified density of the second phase to correct at least some of the second property measurements, such as to correct water content measurements from a electrical characterization apparatus 190. Then, the method of FIG. 4 can calculate a first determination of the first phase fraction (step 416) using the corrected second property measurements. Then, the method of FIG. 4 can calculate a property of the first phase, such as the density of water (step 418) and use that value to calculate a second determination of the first phase content (step 420). In one embodiment, the method can compare the first determination 416 to the second determination 420 in step 422. In one embodiment, the fraction of the first phase by both determinations can be stored and outputted (step 424), and displayed (step 426).

Figure 5:
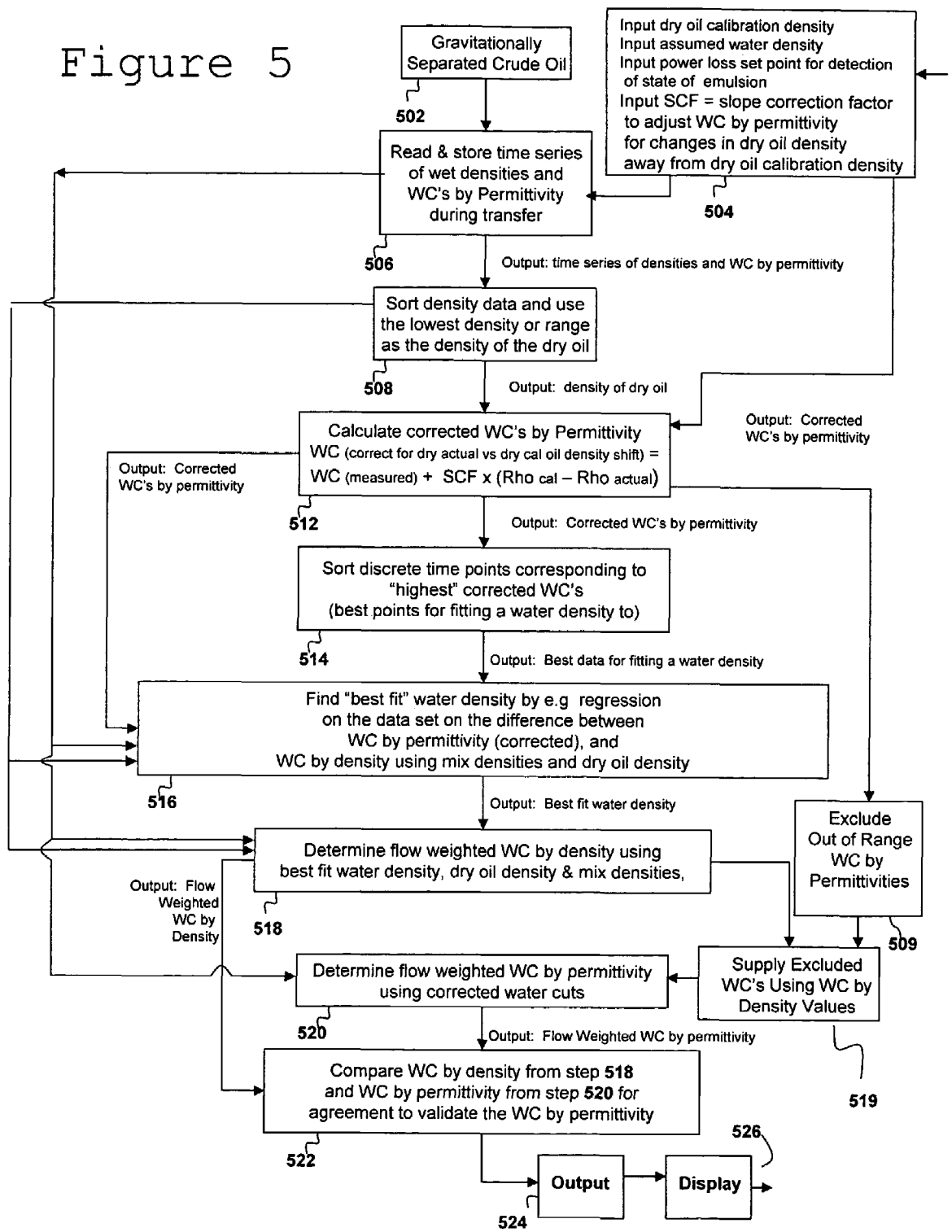
FIG. 5 shows another embodiment of a method used in the system of FIG. 1 and FIG. 1B for determining and validating the water cut of crude petroleum oil that has been subjected to gravitationally-induced separation, consistent with a preferred embodiment.

FIG. 5 shows an exemplary method for determining and validating the water cut of crude petroleum oil according to the method of FIG. 5. The method of FIG. 5 is applied to a batch of gravitationally separated crude petroleum oil (step 502) as might be the case in the transfer of crude petroleum oil that has been stored in tank 233 after being pumped from production gas-liquid separator 228. In one embodiment, reference values, parameters, data sets, and/or equations which have been fitted to those values or data sets are inputted for use in the development of corrective transforms by computer or microprocessor system 172 (step 504). The method of FIG. 5 requires that the on-line electrical characterization apparatus 190 electrical measurements of water content be read and collected (step 506). The method of FIG. 5 requires densitometer measurements of the mixture density and the flow rates of the crude petroleum oil stream measured by the on-line densitometer 192 are read and stored (step 506). All of these values can then be stored in the memory of the computer or microprocessor system 172 and then be used to implement data transformation methods. In one embodiment, the values can also be communicated to an external system 174 via link 196 for various operations such as storage, processing, data manipulation, transform development, and correction of raw data via the transforms by implementing the method of FIG. 5 on external system 174. In one embodiment, step 508 can sort the density data from the densitometer and identifies the lowest density value, or it can take an average of the lowest densities, for example, an average of the lowest 1% to 10%. In step 508, the method of FIG. 5 can use this value as the density of the actual dry oil phase. In one embodiment, step 512 can calculate a corrected water cut by permittivity by calculating the difference between the calibration dry oil density and the value assigned as the actual dry oil density in step 508. In one embodiment, step 512 can then multiply this difference times the slope correction factor inputted in step 504. In one embodiment, step 514 can then sort the corrected water cuts from step 512 to produce a set of highest water cuts from which to best-fit a density of the water phase to. Step 516 can then calculates a best-fit water density using the set of data from step 514, the wet densities generated in step 506, and the dry oil density value assigned in step 508. The method of FIG. 5 can then determine a flow weighted water cut by density using the flow rates and densities from step 506, the best fit water density from step 516, and the assigned dry oil density from step 508. The method of FIG. 5 then determines a flow weighted corrected water cut by permittivity using the corrected water cuts from step 512 and the flow rates from step 506. Note that if the water cut by permittivity is beyond the range of the maximum water cut that can be determined by electrical characterization apparatus 190, then that data can be excluded from the flow weighted average water cut by permittivity by step 507 and any missing water cut's can be supplied by using water cuts from step 518 via step 519. The method of FIG. 5 can then compare the water cut by permittivity determination from step 520 and can compare it to the water cut by density determination from step 518 to validate the water cut by permittivity in step 522. The corrected and validated water cut by permittivity and the water cut by density can be outputted (step 524), which, in one embodiment, includes corrected electrical property characterization such as WC by permittivity. In one embodiment, flow weighted averages for the fraction of the first and second components are displayed (step 526).

EXAMPLE 1

Figure 6:
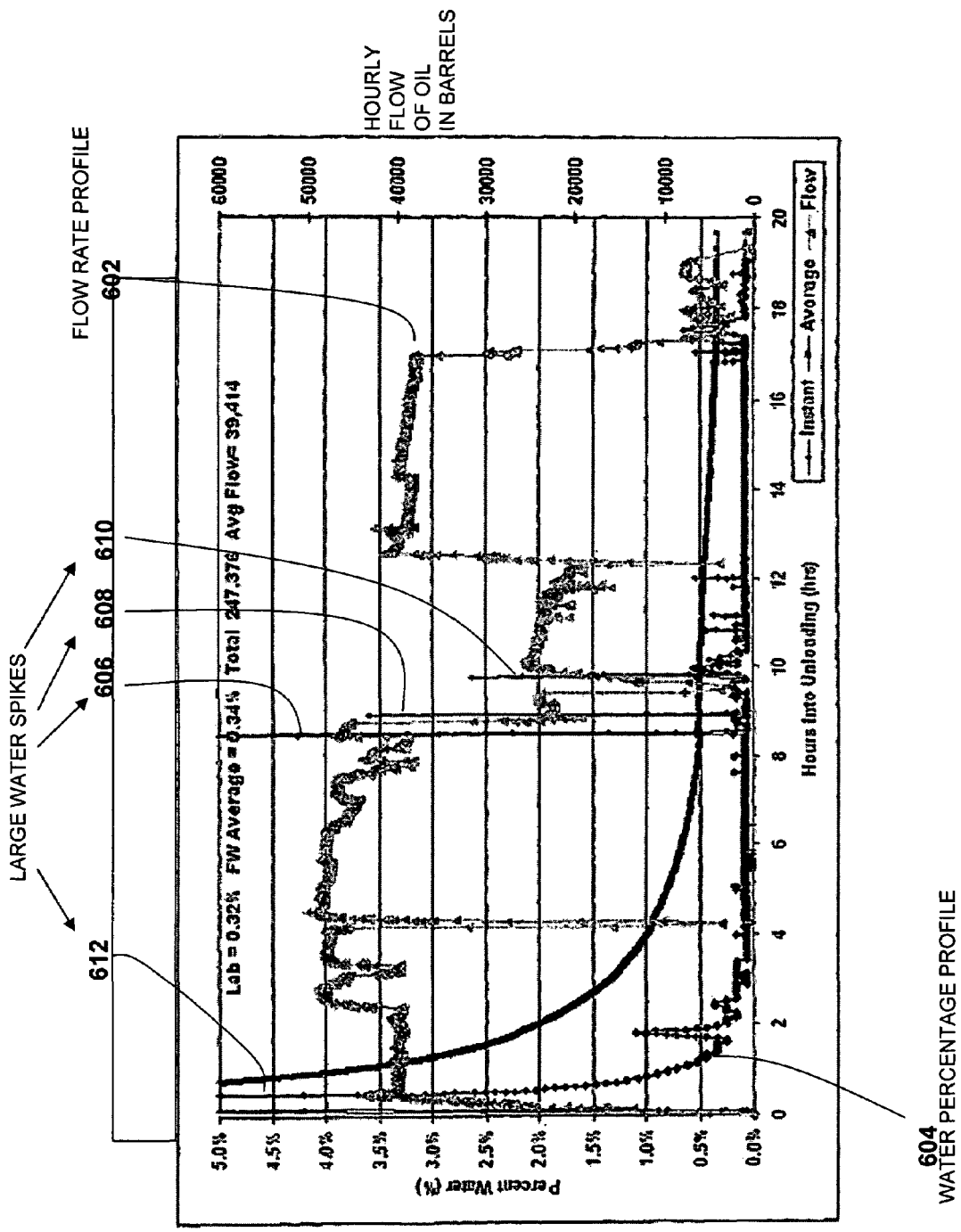
FIG. 6 shows an example of an oil tanker ship unloading flow rate profile and water cut profile in which 247,376 barrels of medium crude petroleum oil were unloaded over about 20 hours.
Figure 6A:
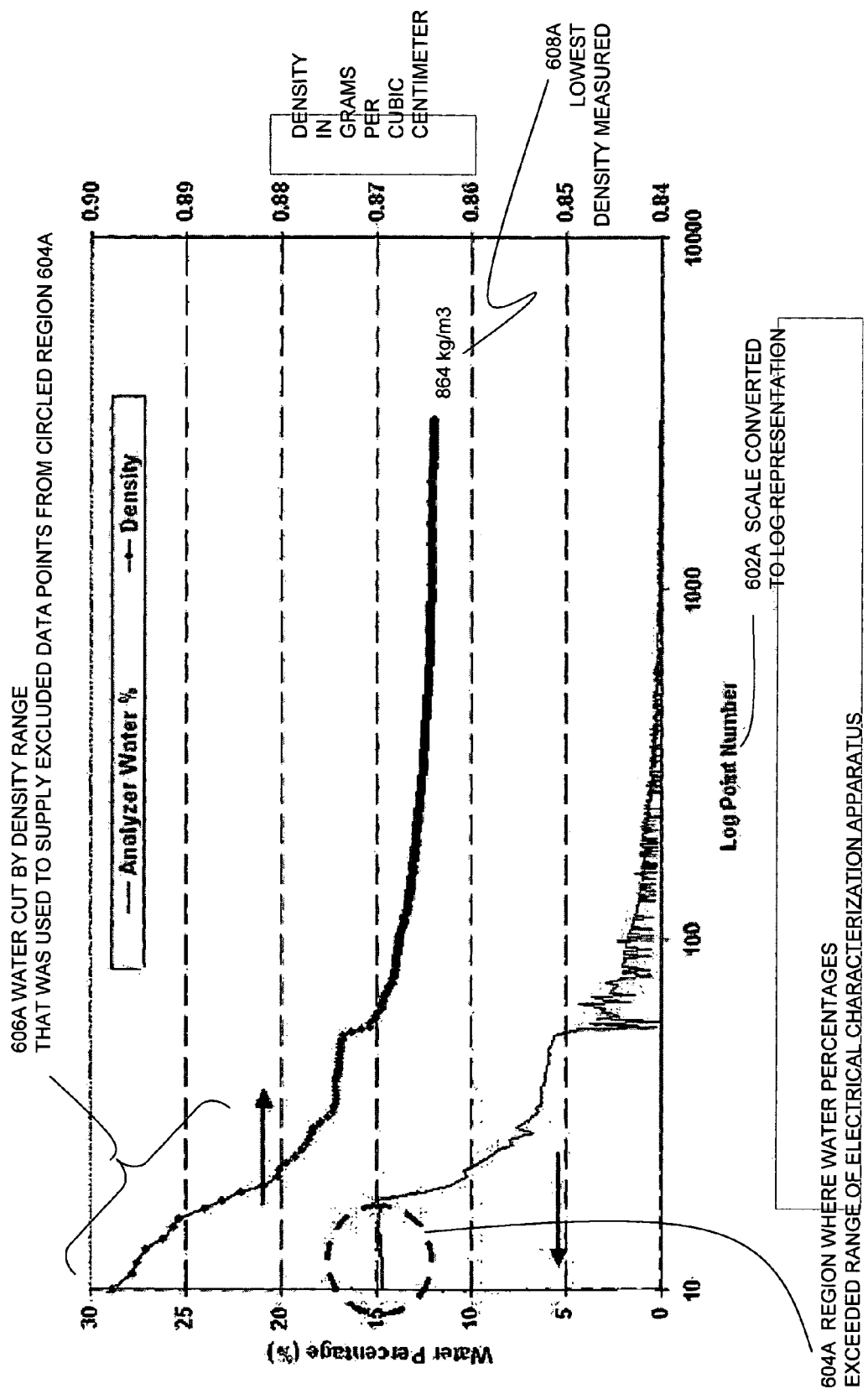
FIG. 6A shows data from the same ship unloading event with the no flow rate data points removed and the remaining data sorted by density.
Figure 6B:
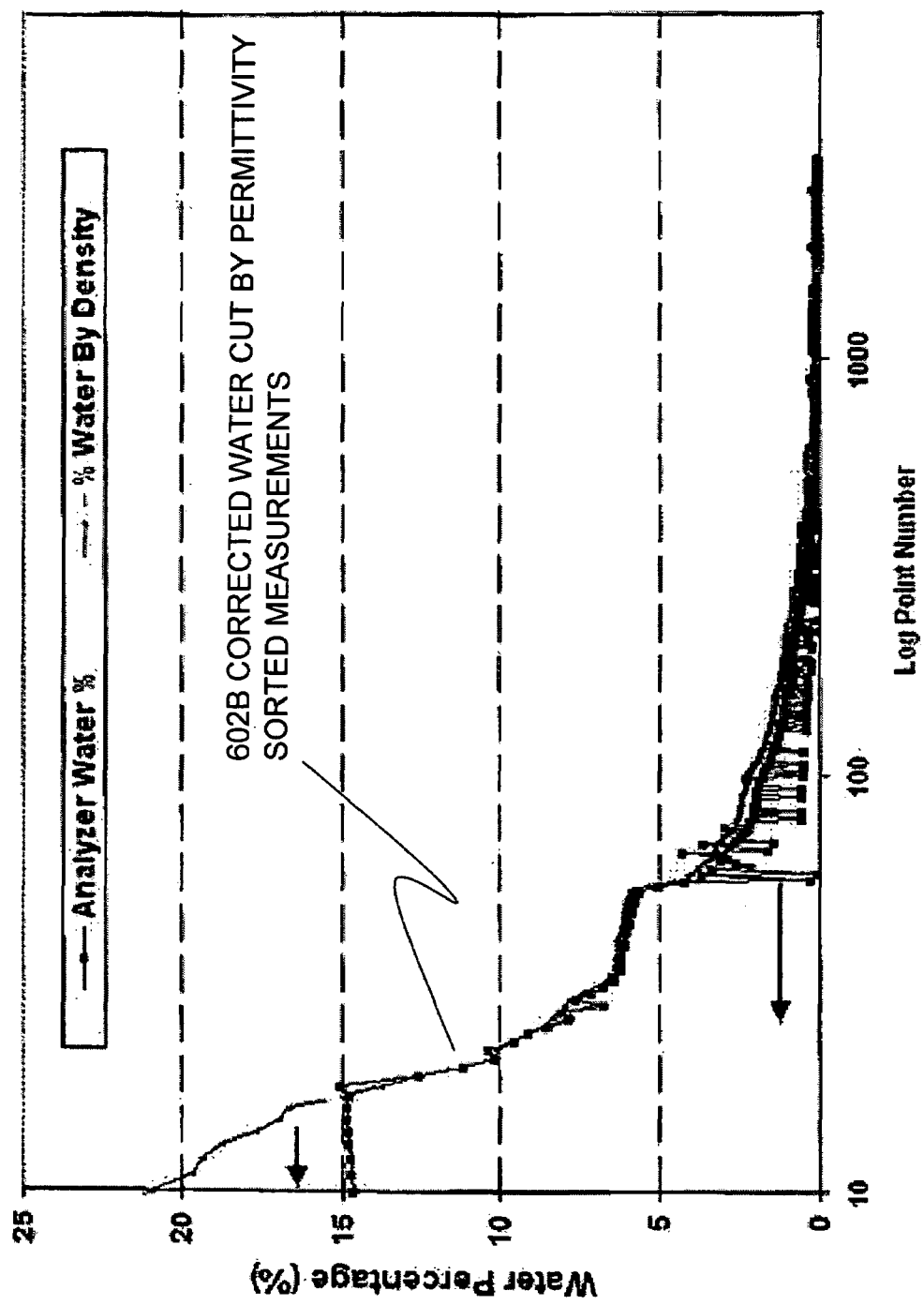
FIG. 6B shows data from the same ship unloading event where both water cut by density and water cut by permittivity are shown.

As an illustrative, non-limiting example, a preferred embodiment of the present invention can be applied to determine the water cut in 247,376 barrels of crude petroleum oil being off-loaded from an oil tanker 237. In this example, system 150 used the method of FIG. 5 and was located at point 239. An auto-sampler 226B was also present and the sample from the off-loading was analyzed using Karl Fischer titration as previously described, and arrived at a value of 0.32% water. In the ship unloading profile of FIG. 6, the flow started and stopped as shown in line 602, ran at half the rate for several hours, and had some very large spikes of water content in the oil, as shown in line 604, at points 606, 608, 610, and 612. Data was collected as per step 506. In normal ship unloading, it is expected to see water contents above 5% at some times during the unloading process FIG. 6A is the same unloading event with the no flow rate cases removed and the remaining data sorted by density per step 508, and displayed as a log point number, as shown by highlight arrow 602A. The lowest density measured, 864 kg/m$^3$, is shown as point 608A per step 508, and this would be assigned the as the value of the actual dry oil density per step 508. Note that this value compared favorably to an offline laboratory determined value of 867 kg/m$^3$. This value is then used to perform the corrected water cuts by permittivity determination of step 512 and are show as line 602B on FIG. 6B. Circled region 604A on FIG. 6A is where the water percentages exceeded the range of the electrical characterization apparatus 190, were excluded as invalid data per step 507, and therefore demonstrate how high the water can actually be at times during the unloading of a cargo ship. Note that in the flow weighted average calculation of corrected water cut by permittivity step 520, water cuts for excluded data points can be supplied from the water cut by density calculation of step 518 via step 519, shown as 606A on FIG. 6A.

Using valid corrected water cuts by permittivity in the range of 0.50% to 5% supplied by step 514, a data set was prepared to determine a best fit of a water density value in step 516 using, for example, a simple iterative process. This water density was found to be 1025 kg/m3, which is close to the water density expected from the region where the crude petroleum oil originated from in Alaska. This value was used to calculate the flow-weighted water cut by density per step 518 which was 0.43%. Step 520 calculated the flow-weighted water cut by permittivity and arrived at a value of 0.34%, which is close to the offline titration value of 0.32% previously disclosed. Thus, all three methods arrived at similar results. Further, even though the water by density of 0.43% was higher than the other values, it confirmed that the analyzer provided a reasonable result. Without a water cut by density result, there is only one other comparison to be made and that is with the laboratory. If the sample had been improperly handled and a lab result of 0.00% was obtained, then the water cut by density value would, for example, raise the question of the lab potentially being incorrect.

EXAMPLE 2

This example is the generally the same experimental design as Example 1 except that heavy crude petroleum oil (API density of 21 degrees) was used instead of light crude petroleum oil (API density of 32 degrees) because it was known that this crude was from Argentina with a history of this density.

Figure 7:
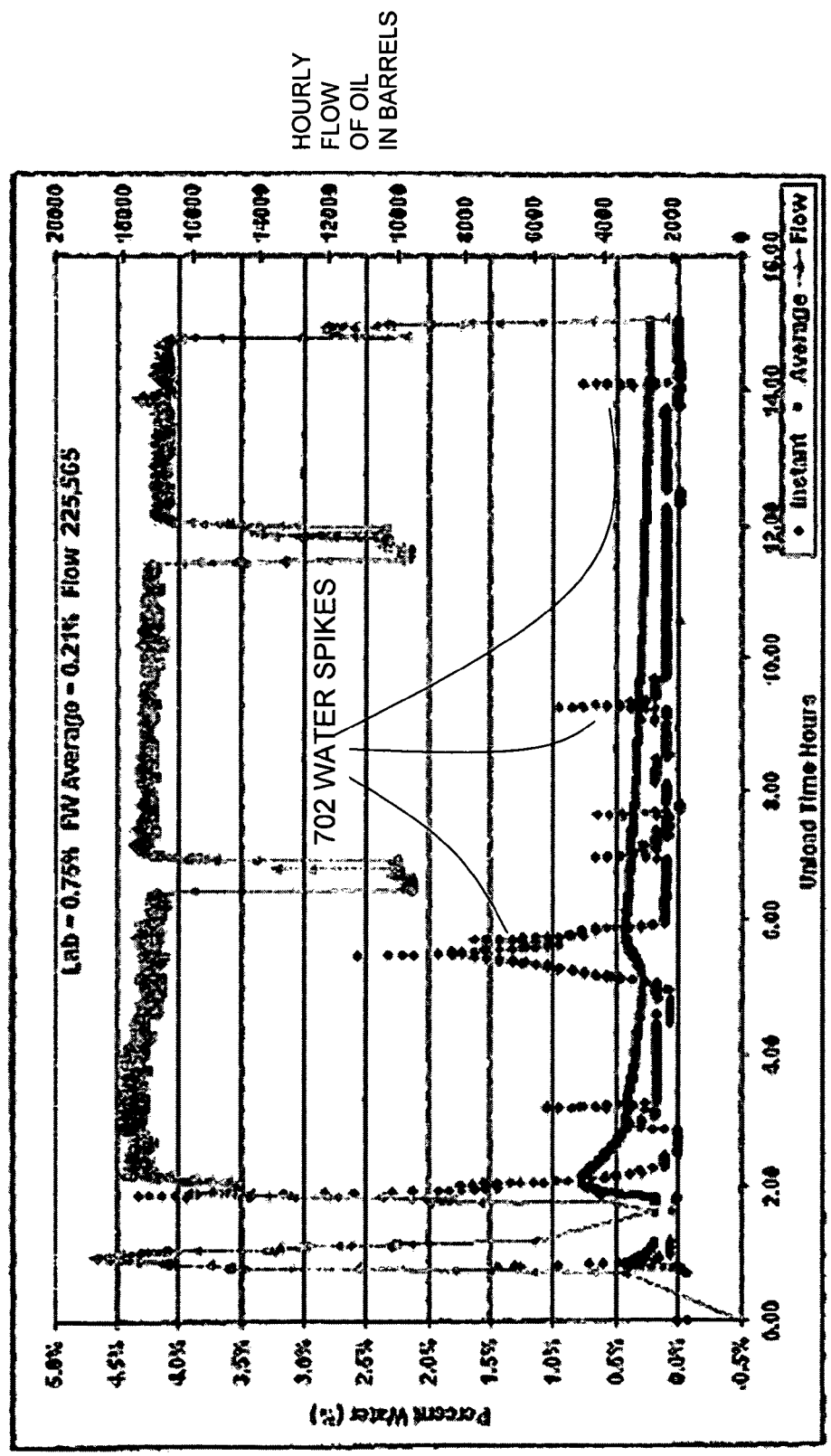
FIG. 7 shows another example of an oil tanker ship unloading flow rate profile and water cut profile in which 225,565 barrels of heavy crude petroleum oil were unloaded over about 15 hours.
Figure 7A:
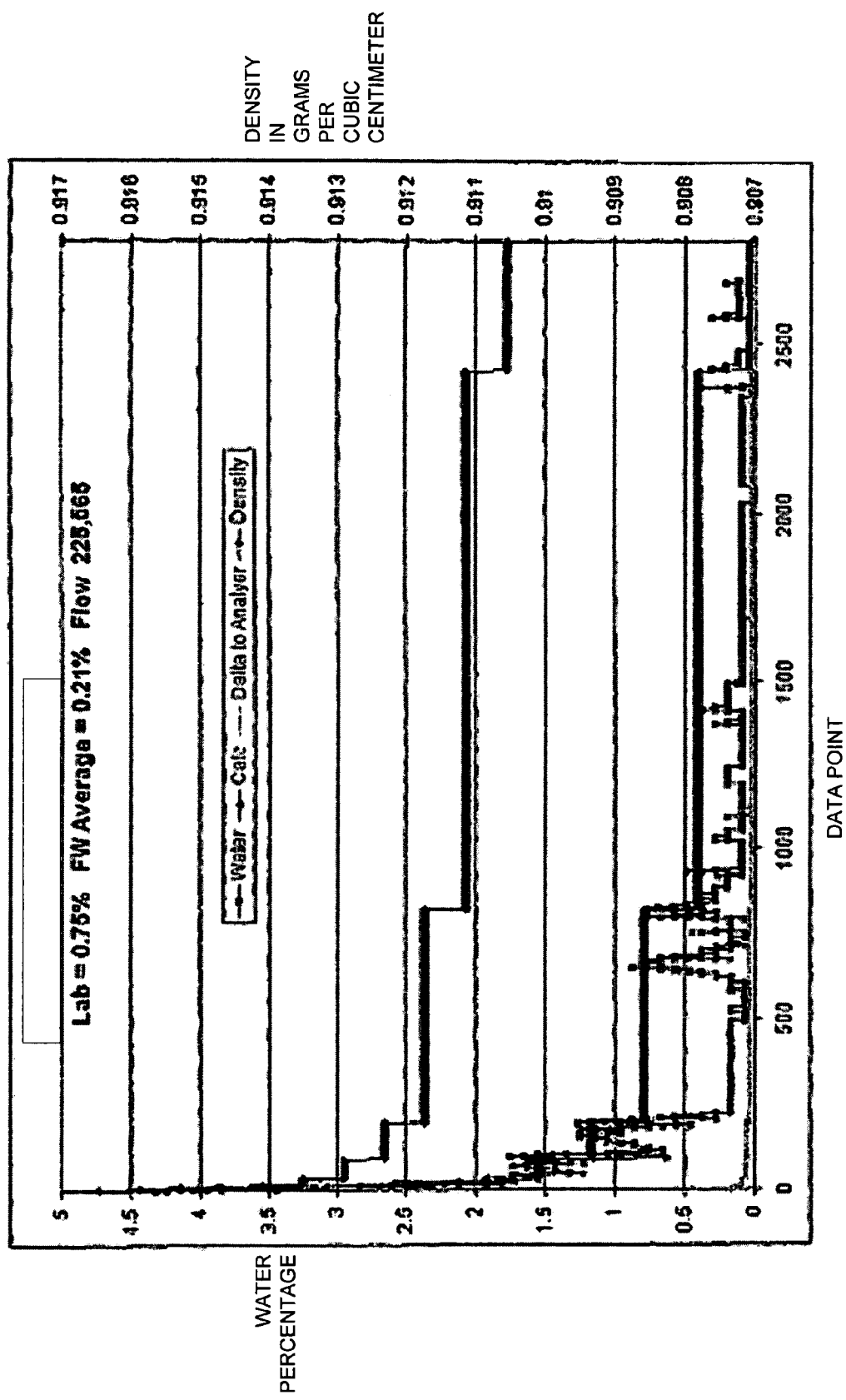
FIG. 7A shows data from the same ship unloading event as FIG. 7 with the data sorted by density for both density and water cut by permittivity.

A total of 225,565 barrels of oil were transferred from a ship as shown in FIG. 7 over a 15 hour period. During the unloading, spikes of water content 702 can be seen on the instantaneous water cut from electrical characterization apparatus 190. FIG. 7A shows the sorted densities per step 508 and the sorted water cuts corrected for the density of the oil shipped per step 514. The flow-weighted average water cut by permittivity was 0.21% per step 520. The flow-weighted average water cut by density was 0.47% per step 518. The composite water cut by offline titration was 0.75%. Later, it was found that the titration value of 0.75% water was an invalid number due to interference with the titration chemistry from components naturally present in the crude petroleum oil.

Thus, the water cut by permittivity was validated by the WC by density when the values were compared per step 522. Without the benefit of the validation of WC by density, since the titration value was so high, the question would have been asked as to whether there was a problem with the laboratory titration procedure and results, or with the WC by permittivity determination. One response to the question would be to perform a centrifuge method off-line analysis on the sample from the composite sampler. But, if no comparison had been made, e.g. not prompted by the validation using both the WC by density and permittivity, the sample would have been destroyed and there would have been no possibility of finding the interference with the Karl Fischer titration.

According to a disclosed class of innovative embodiments, there is provided a method for determining a first phase fraction of a multiphase fluid, comprising the actions of (a) collecting a plurality of measurements on at least a gravitationally-separated portion of the fluid, and identifying at least one said measurement as corresponding to a second phase of the fluid; (b) exploiting said identified measurement to correct the values of other ones of said plurality of measurements; and (c) calculating and outputting the fraction of said first phase of the multiphase fluid using at least some of said corrected values of said plurality of measurements.

According to a disclosed class of innovative embodiments, there is provided a method for making and validating a determination of the aqueous fraction of an oily multiphase fluid, comprising the actions of (a) collecting a series of density and electrical property measurements across multiple samples of at least a gravitationally-separated oily portion of the fluid; (b) identifying the density of the oily component of the fluid; (c) exploiting said identified density to correct at least some of said electrical property measurements, and making a first determination of the aqueous fraction therewith; (d) using ones of said corrected electrical property measurements to calculate the aqueous phase density, and making a second determination therewith; and (e) generating and outputting a confirmation of a validation if said determinations are adequately matched.

According to a disclosed class of innovative embodiments, there is provided a multiphase fluid characterization system, comprising a densitometer which measures the density of an oily and aqueous multiphase fluid flow stream sourced from a gravitationally-separated multiphase fluid; an electrical characterization stage which makes one or more electrical property measurements of the flow stream; and a logic circuit which collects a time series of measurements from said densitometer and said electrical characterization stage, identifies the density of the oily component of the fluid, uses said identified density to correct at least some of said electrical property measurements, makes a first determination of the aqueous fraction, uses ones of said corrected electrical property measurements to calculate the aqueous phase density, make a second determination of said aqueous fraction, and generates and outputs a confirmation of a validation if said determinations are adequately matched.

Modifications and Variations

As will be recognized by those skilled in the art, the innovative concepts described in the present application can be modified and varied over a range of applications, and accordingly the scope of patented subject matter is not limited by any of the specific exemplary teachings given. It is intended to embrace all such alternatives, modifications, and variations that fall within the spirit and broad scope of the appended claims.

The methods and systems of the present application can operate across a wide range of processing situations and conditions. One of ordinary skill in the art, with the benefit of this disclosure, will recognize the appropriate use of the methods and systems for a chosen application of a given or dynamic set of operating parameters, including process pressure, process temperature, process flow rate, multiphase fluid composition, aqueous phase composition, non-aqueous-phase composition, presence of condensible gases, presence of non-condensible gases, use of flow stream conditioning operations prior to characterization, flow stream pipe location, slip-stream installation versus full-stream installation versus insertion installation, characterization apparatus or system location, ambient temperature, or other conditions, or combinations thereof.

Optionally, the methods and systems of the present application can be configured or combined in various schemes. The combination or configuration depends partially on the required measuring precision and accuracy and the operational envelope of the process. One of ordinary skill in the art, with the benefit of this disclosure, will recognize the appropriate combination or configuration for a chosen application.

Optionally, the methods and systems of the present application may also take the temperature and pressure of the multiphase fluid or single phase fluids in streams 152, 171, 162, 176, and 170, the density of a gas stream in stream 162, the liquid level in separator 160, and any flags such as separator level out of range which may define the reliability of the data or provide variables to use for analysis. One of ordinary skill in the art, with the benefit of this disclosure, will recognize the appropriate additional measurements that would be beneficial for a chosen application. Optionally, such measurements taken by the methods and systems of the present application may also be sent to the external computer or microprocessor system 174 for processing. For example, if the gas density exceeds a certain amount, this fact can be used to flag improper data due to liquids carrying over into the gas from the separator during a system upset such as slugging. Liquid density having a large standard deviation beyond a preset level can be used for the same determination. This would be due to gas carry under into the liquids, which would make the liquid density very noisy.

Optionally, gravitationally-induced separation of crude petroleum oil can be accelerated by pre-treating a crude petroleum oil stream flowing into a storage vessel by using any emulsion pre-treating techniques, including chemical, electrical, and mechanical methods, or combinations thereof, known to a person having ordinary skill in the art of crude petroleum oil emulsions.

Optionally, multiphase fluid temperature compensation can be employed used to adjust for shifts in temperature using reference data sets relating temperature change to total fluid density change, or curves fitted to such reference data. Optionally, because the thermal expansion of an oil continuous dispersion is generally different than the thermal expansion of a water-continuous dispersion, different reference data sets or curves fitted to such data sets may be employed. Optionally, because the coefficient of thermal expansion for aqueous solutions and non-aqueous solutions differ, calculation routines can use the measured first phase fraction to better adjust for such temperature shifts. One of ordinary skill in the art, with the benefit of this disclosure, will recognize the appropriate systems to employ for such temperature compensation methods.

Optionally, the measurement or measurements identified as corresponding to a second phase of the fluid, e.g. the oil continuous phase, can be exploited in a number of ways. These include the loading of constants into a transform for correcting other data or measurements or calculations, the derivation of non-linear parameters for use in such transforms, the establishment of clipping parameters, use in a lookup table or table of transforms, or other such uses as are known to a person having ordinary skill in the art of data manipulation. Further, methods of exploiting can include the use of box car calculations, filtering, non-linear filtering, matrix calculations, time domain analyses, regression, best fit analyses, or other such calculation methods as known to a person having ordinary skill in the art of the computational sciences.

The configuration of components in FIG. 1 is not the only system capable of performing multiphase fluid characterization on multiphase fluids when they been subjected to gravitationally-induced separation. For example, a gas phase may not be present at all, reducing or eliminating the need for the gas-liquid separator 160. For another example, system 150 might not need components 154, 156, 158, 160, 164, 166, 168, and/or 194, or various combinations thereof. The particular requirements of system 150 would be determined by a particular application as known to one having ordinary skill in the art of instrumentation applications to chemical or petroleum processing.

The electrical characterization apparatus depicted in FIG. 1B is not the only apparatus that can perform the required electrical characterizations of the present innovations. For example, capacitance probes and radio frequency probes can also be adapted top provide the necessary measurements are known to a person having ordinary skill in the art of electrical characterizations of fluids.

The petroleum system of FIG. 2 is not the only system to which the present innovations can be applied to. For example, the present innovations could be applied to a system as simple as a multiphase fluid in a single un-agitated storage tank with a drain on the bottom of the tank through which the multiphase fluid is drained characterized by system 150 using the methods of the present innovations.

Optionally, methods such as the methods of FIGS. 3, 4, 5, and/or the present innovations can include a cross-check step for phase state detection by the electrical characterization apparatus 190 using water cut by density values from the densitometer 192. Specifically, if apparatus 190 chose the wrong phase state and calculated a WC by permittivity, of say, 40%, and densitometer 192 calculated a WC by density of say 85%, it is known to those of ordinary skill in the art of densitometer design and operation that a densitometer does not misread and miscalculate a mixture WC by density of more than a few percent error. Therefore, in this instance, apparatus 190 most likely chose the wrong phase and that particular data point can be recalculated using the other phase as the basis for the re-calculation. Appropriate routines can be worked into such a method to account for this situation.

Optionally, methods such as the methods of FIGS. 3, 4, 5, and/or the present innovations can include a subroutine incorporating the teaching of Scott'3613 to account for uncertainties in oil-continuous dispersions of less than about 5% WC.

Optionally, examples of suitable hardware which can be fully or partially modified to fully or partially embody the methods and systems of the present application include those that are commercially available from Phase Dynamics of Richardson, Tex., under the name known to the industry as Compact Cyclone Multiphase Meter ("CCM").

Optionally, the systems of the present application may not be located in a pipe or conduit. In one class of embodiments, the physical property measuring component and the electrical property measuring component may be located via an insertion installation in a vessel such as a storage tank, mixing tank, accumulator, separator, liquid-liquid contactor, or other processing device for which a multiphase fluid characterization is required. One of ordinary skill in the art, with the benefit of this disclosure, will recognize the appropriateness of the methods and systems of the present application for a chosen application.

Optionally, the systems of the present application can include a sampling port for comparison of the on-line determinations of the first phase fraction with an off-line determination.

Optionally, the pre-determined selection criterion of the present application to identify measurements corresponding to a particular phase may not only be predetermined values of particular measurements or calculations to trigger selection of the measurements, but the criterion may be a sub-routine of equations, comparisons, noise reduction, or other data manipulation techniques. One of ordinary skill in the art of data manipulation, with the benefit of this disclosure, will recognize the appropriateness of such sub-routine options.

Optionally, the methods of the present application can also be embodied in a set of instructions that can be used on a general purpose desktop or laptop computer or microprocessor system, such as external system 174. The set of instructions can comprise input instructions that receives data from flow computer or microprocessor system 172. Similarly, the input instructions can accept instructions from a user via one or more input devices, such as a keyboard, mouse, touchpad, or other input device. The instructions can also implement the methods of the present invention or any part thereof to generate, for example, an updated transform for the calculation of first phase fraction by either the density method or the permittivity method. The instructions can cause the computer or microprocessor system to display information, such as the results of the methods of the present invention, to a user, through a display monitor, printer, generated electronic file, or other such device. The instructions can also cause the computer or microprocessor system to transmit the results to a distant user via modem, cable, satellite, cell link, and/or other such means. For such digital communications, RS-422 or RS-485 can optionally be used to allow links from flow computer or microprocessor system 172 or external system 174 to multiple external units. Optionally, a 4-20 milliamp analog output signal can be used to allow external processing of the system measurements.

Optionally, the methods of the present invention can also be embodied in a computer readable medium.

Additional general background, which helps to show variations and implementations, may be found in the following publications, all of which are hereby incorporated by reference:

(1) Bentley N. Scott, Proceedings of IPC 2004 International Pipeline Conference, Calgary, Alberta, Canada, "Uncertainties in Pipeline Measurement", IPC04-0046, Oct. 4-8, 2004.

(2) Bentley N. Scott, Larry Baker, and Dr. Bjornar Svingen, 16$^{th}$ North Sea Flow Measurement Workshop 1998, "Well Testing Issues and a New Compact Cyclone System."

(3) Compact Cyclone Multiphase Meter (CCM) Specifications Sheet, CCM Literature 0205, available on the Web at http://www.phasedynamics.com, (last visited Jul. 1, 2006).

(4) Family of Water Cut Analyzers, Analyzer Family 0306, available on the Web at http://www.phasedynamics.com, (last visited Jul. 1, 2006).

None of the description in the present application should be read as implying that any particular element, step, or function is an essential element which must be included in the claim scope: THE SCOPE OF PATENTED SUBJECT MATTER IS DEFINED ONLY BY THE ALLOWED CLAIMS. Moreover, none of these claims are intended to invoke paragraph six of 35 USC section 112 unless the exact words "means for" are followed by a participle.

The claims as filed are intended to be as comprehensive as possible, and NO subject matter is intentionally relinquished, dedicated, or abandoned.

What is claimed is:

1. A method for determining a first phase fraction of a multiphase fluid, comprising the actions of:
    collecting a plurality of measurements, using at least one measurement sensor and no reference sensor, on at least one gravitationally-separated portion of the fluid corresponding to at least a second phase of the fluid, and identifying at least one said measurement as corresponding to the second phase of the fluid based on a measurement minima;
    exploiting said identified measurement corresponding to the second phase of the multiphase fluid to correct the values of other ones of said plurality of measurements corresponding to at least the first phase and the second phase of the multiphase fluid; and
    calculating and outputting the fraction of said first phase of the multiphase fluid using at least some of said corrected values of said plurality of measurements by applying a derived corrective transform to the plurality of measurements covering all of the gravitationally- separated portions to thereby correct said measurements using hindsight determination.

2. The method of claim 1 wherein the multiphase fluid is crude petroleum oil, the first phase is a water-continuous phase, and the second phase is an oil-continuous phase.

3. The method of claim 1 wherein said plurality of measurements include the densities of an oily multiphase fluid and water percentages of the same oily multiphase fluid;
    wherein said identified measurement is the dry oil density;
    wherein water percentages of the multiphase fluid by the permittivity method are corrected;
    wherein flow-weighted water percentages of the multiphase fluid by the density method are calculated; and
    wherein a flow-weighted average of said corrected water percentages by the permittivity method is used to calculate the water fraction in the crude petroleum oil.

4. The method of claim 1, wherein said measurements include electrical properties measured by a microwave oscillator load pull device.

5. The method of claim 1, further comprising the additional step of filtering said measurements.

6. The method of claim 1, wherein said step of determining correct fluid properties is additionally based on stored data that has been obtained by means other than by means of claim 1.

7. The method of claim 1, wherein said measurements are at least partly determined from calculations.

8. The method of claim 1 wherein the multiphase fluid is a gravitationally-separated crude petroleum oil transferred from one point to another, and a time series of discrete time points of said plurality of measurements is collected during the transfer.

9. The method of claim 8, wherein points in said series are not equally spaced.

10. The method of claim 8, further comprising the additional step of performing a regression calculation on the plurality of measurements collected during the transfer for use in determining a weighted water cut.

11. A method for making and validating a determination of the aqueous fraction of an oily multiphase fluid, comprising the actions of:
    collecting a series of density and electrical property measurements across multiple samples of a gravitationally-separated oily portion of the fluid using only a measuring sensor;
    identifying the density of the oily portion of the fluid;
    exploiting said identified density to correct at least some of said electrical property measurements that includes a first determination of the aqueous fraction therewith;
    using ones of said corrected electrical property measurements to calculate the aqueous phase density that includes a second determination therewith; and
    generating and outputting a hindsight confirmation of a validation if said determinations are adequately matched and automatically correcting said determinations.

12. The method of claim 11, wherein said measurements include electrical properties measured by a microwave oscillator load pull device.

13. The method of claim 11, further comprising the additional step of filtering said measurements.

14. The method of claim 11, wherein said step of determining correct fluid properties is additionally based on stored data that has been obtained by means other than by means of claim 11.

15. The method of claim 11, wherein said measurements are at least partly determined from calculations.

16. The method of claim 11 wherein the crude petroleum oil is a particular lot of crude petroleum oil that will be, has been, or is being transferred from one point to another, and a time series of discrete time points of said plurality of measurements is collected during the transfer.

17. The method of claim 16, wherein points in said time series are not equally spaced.

18. The method of claim 16, further comprising the additional step of performing a regression calculation on the plurality of measurements collected during the transfer for use in determining a weighted water cut.

19. A multiphase fluid characterization system, comprising:
    a densitometer which measures the density of an oily and aqueous multiphase fluid flow stream sourced from a gravitationally-separated multiphase fluid;
    an electrical characterization stage which makes one or more electrical property measurements of the flow stream; and
    a logic circuit which collects a time series of measurements only from said densitometer and said electrical characterization stage covering discrete time points in said stream and storing said measurements in a memory, identifies the density of the oily component of the fluid at each discrete time based on a minima measurement, uses said identified density to correct at least some of said electrical property measurements, makes a first determination of the aqueous fraction, uses ones of said corrected electrical property measurements to calculate the aqueous phase density measurements, make a second determination of said aqueous fraction, and generates and outputs a confirmation of a validation if said determinations are adequately matched in the totality of the flow stream using the collected measurements.

20. The system of claim 19, wherein said electrical property measurements include electrical properties measured by a microwave oscillator load pull device.

21. A method for determining the water in a first phase fraction of crude petroleum oil multiphase fluid, comprising the actions of:
    a) collecting a plurality of density and water percentage measurements on at least a gravitationally-separated portion of crude petroleum oil multiphase fluid, and identifying at least one said density measurement as corresponding to dry oil of a second phase of the fluid based on a minima measurement;

b) exploiting said identified measurement to correct the values of other ones of said plurality of water percentage measurements of the gravitationally-separated portions of crude petroleum oil multiphase fluid by the permittivity method; and c) calculating and outputting the flow weighted water fraction of said crude oil first phase of the multiphase fluid using at least some of said corrected values of said plurality of measurements for hindsight correction of said measurements, wherein the correction can operate using measurements from only a single density sensor.

* * * * *